(12) United States Patent
Shuber et al.

(10) Patent No.: US 6,566,101 B1
(45) Date of Patent: *May 20, 2003

(54) PRIMER EXTENSION METHODS FOR DETECTING NUCLEIC ACIDS

(76) Inventors: Anthony P. Shuber, 11 Grant St., Milford, MA (US) 01757; Stanley N. Lapidus, 12 Old Evergreen Rd., Bedford, NH (US) 03110

(*) Notice: Subject to any disclaimer, the term of this patent is extended or adjusted under 35 U.S.C. 154(b) by 0 days.

This patent is subject to a terminal disclaimer.

(21) Appl. No.: 09/067,212

(22) Filed: Apr. 27, 1998

Related U.S. Application Data

(63) Continuation-in-part of application No. 08/877,333, filed on Jun. 16, 1997, now Pat. No. 5,888,778.

(51) Int. Cl.$^7$ .............. C12P 19/34; C12Q 1/68; G01N 33/00; C07H 21/02; C07H 21/04

(52) U.S. Cl. .............. 435/91.2; 435/6; 435/91.1; 436/94; 536/23.1; 536/24.3; 536/24.33

(58) Field of Search .............. 435/6, 91.1, 91.2, 435/183, 283.1, 287.1, 287.2; 536/23.1, 24.33, 25.3, 24.3, 24.32; 436/94

(56) References Cited

U.S. PATENT DOCUMENTS

| | | | |
|---|---|---|---|
| 5,202,231 A | 4/1993 | Drmanac et al. | 435/6 |
| 5,545,527 A | 8/1996 | Stevens et al. | 435/6 |
| 5,552,283 A | 9/1996 | Diamandis et al. | 435/6 |
| 5,571,676 A | 11/1996 | Shuber | 435/6 |
| 5,578,458 A | 11/1996 | Caskey et al. | 435/6 |
| 5,589,330 A | 12/1996 | Shuber | 435/5 |
| 5,591,582 A | 1/1997 | Bos et al. | 435/6 |
| 5,610,287 A * | 3/1997 | Nikiforov et al. | 536/24.3 |
| 5,627,032 A | 5/1997 | Ulanovsky | 435/6 |
| 5,846,710 A | 12/1998 | Bajaj | 435/6 |
| 5,885,775 A | 3/1999 | Haff et al. | 435/6 |
| 5,888,778 A * | 3/1999 | Shuber | 435/91.1 |
| 6,013,431 A * | 1/2000 | Soderlund et al. | 435/5 |

FOREIGN PATENT DOCUMENTS

| | | |
|---|---|---|
| EP | 0 332 435 B1 | 9/1989 |
| EP | 0 332 435 A2 | 9/1989 |
| EP | 0 408 918 B1 | 1/1991 |
| EP | 0 408 918 A1 | 1/1991 |
| EP | 0 497 527 A1 | 8/1992 |
| WO | WO 90/09455 A | 8/1990 |
| WO | WO 91/13075 | 9/1991 |
| WO | WO 92/15712 | 9/1992 |
| WO | WO 92/16657 A | 10/1992 |
| WO | WO 94/23055 A | 10/1994 |
| WO | WO 95/00669 | 1/1995 |
| WO | WO 95/12607 | 5/1995 |
| WO | WO 96/30545 | 10/1996 |
| WO | WO 97/09449 A | 3/1997 |
| WO | WO 97/23651 A | 7/1997 |
| WO | WO 98/58084 A | 12/1998 |

OTHER PUBLICATIONS

Ugozzoli et al., Detection of specific alleles by using allele-specific primer extension followed by capture on solid support. Gata, 9, 107–112, 1992.*

(List continued on next page.)

*Primary Examiner*—Ethan C. Whisenant
*Assistant Examiner*—Frank Lu

(57) ABSTRACT

Methods are provided for selective nucleic acid sequence detection in single base primer extension reactions of high sensitivity. These methods are useful for detecting small amounts of mutant nucleic acid in a heterogeneous biological sample. These methods are particularly useful for identifying individuals with gene mutations indicative of early colorectal cancer.

24 Claims, 3 Drawing Sheets

OTHER PUBLICATIONS

Schumaker et al., Mutation detection by solid phase primer extension. Human Mutation, 7, 346–354, 1996.*

Carothers et al., Point mutation analysis in a mammalian gene: rapid preparation of total RNA, PCR amplification of cDNA, and Taq sequencing by a novel method. Biotechniques, 7, 494–496, 498, and 499.*

Canard et al., "DNA polymerase fluorescent substrates with reversible 3'-tags," GENE, 148, pp. 1–6, 1994.*

Caetano–Anollés (1993) Amplifying DNA with Arbitrary Oligonucleotide Primers, *PCR Methods and Applications, 3:85–94.*

Krook, et al., (1992) Rapid and simultaneous detection of multiple mutations . . . in non–insulin–dependent diabetes, *Human Molecular Genetics, 1:391–395.*

Schumaker, et al., (1996) Mutation Detection by Solid Phase Primer Extension, *Human Mutation, 7:346–354.*

Ikonen, et al., (1992) Quantitative Determination of Rare mRNA Species by PCR and Solid–phase Minisequencing, *PCR Methods and Applications 1:234–240.*

Runnebaum, et al., (1994) Multiplex PCR Screening detects small p53 deletions and insertions in human ovarian cancer cell lines, *Human Genetics, 93:620–624.*

Lebacq, (1992) Polymerase chain reaction and other methods to detect hot–spot and multiple gene mutations, *Ann Biol Clin, 50:709–712.*

Syvänen, (1994) Detection of point mutations in human genes by the solid–phase minisequencing method, *Clinica Chimica Acta, 226:225–236.*

Caldas, et al., (1994) Detection of K–ras Mutations in the Stool of Patients with Pancreatic Adenocarcinoma and Pancreatic Ductal Hyperplasia, *Cancer Research, 54:3568–3573.*

Villa, et al., (1996) Identification of Subjects at Risk for Colorectal Carcinoma Through a Test Based on K–ras Determination in the Stool, *Gastroenterology, 110:1346–1353.*

Hasegawa, et al., (1995) Detection of K–ras mutations in DNAs isolated from feces of patients with colorectal tumors by mutant–allele–specific amplification (MASA), *Onogene, 10:1441–1445.*

Smith–Ravin, et al., (1995) Detection of c–Ki–ras mutations in feacal samples from sporadic colorectal cancer patients, *Gut, 36:81–86.*

Eguchi, et al., (1996) Mutations of the p53 Gene in the Stool of Patients with Resectable Colorectal Cancer, *Cancer Suppl., 77:1707–1710.*

Nollau, et al., (1996) Detection of K–ras Mutations in Stools of Patients with Colorectal Cancer by Mutant–Enriched PCR, *Int. J. Cancer, 66:332–336.*

Kieleczawa, et al., (1992) DNA Sequencing by Primer Walking with Strings of Contiguous Hexamers, *Science, 258:1787–1791.*

Fu, et al., (1995) A DNA Sequencing Strategy That Requires Only Five Bases of Known Terminal Sequence for Priming, *Proc. Natl. Acad. Sci. USA, 92:10162–10166.*

Kotler, et al., (1993) DNA Sequencing: Modular Primers Assembled from a Library of Hexamers or Pentamers, *Proc. Natl. Acad. Sci. USA, 90:4241–4245.*

Fauser, et al., (1997) Simultaneous Detection of Multiple Point Mutations Using Fluorescence–Coupled Competitive Primer Extension, *BioTechniques, 22:964–968.*

Beskin, A.D. et al., "On the Mechanism of The Modular Primer Effect", Nucleic Acids Research, vol. 23, No. 15, Jan. 1, 1995, pp. 2881–2885.

* cited by examiner

PRIMER EXTENSION METHODS FOR DETECTING NUCLEIC ACIDS

This patent application is a continuation-in-part of U.S. Ser. No. 08/877,333, filed Jun. 16, 1997, now U.S. Pat. No. 5,888,778 the disclosure of which is incorporated herein by reference.

FIELD OF THE INVENTION

The present invention relates generally to oligonucleotide primer extension methods for identifying a single nucleotide in a nucleic acid sample. Methods of the invention are useful for disease diagnosis by detecting and identifying the presence of genetic mutations or disease-causing microorganisms in biological samples.

BACKGROUND OF THE INVENTION

The knowledge of molecular defects causative of diseases, such as inherited disorders and cancer, is increasing rapidly. Inherited diseases thought to be caused by genetic mutations include sickle cell anemia, α- and β-thalassemias, phenylketonuria, hemophilia, $α_i$-antitrypsin deficiency, and cystic fibrosis. Sickle cell anemia, for example, is reported to result from homozygosity resulting from a single base pair substitution in the sixth codon of the β-globin gene. Antonarakis, *New England J. Med.*, 320: 153–163 (1989). Mutations in the insulin receptor gene and in the insulin-responsive glucose transporter gene have been detected in insulin-resistant diabetes. Krook et al., *Human Molecular Genetics*, 1: 391–396 (1992).

Cancer has been associated with genetic mutations in a number of oncogenes and tumor suppressor genes. Duffy, *Clin. Chem.*, 41: 1410–1413 (1993). For example, point mutations in the ras genes have been shown to convert those genes into transforming oncogenes. Bos et al., *Nature*, 315: 726–730. Mutations and the loss of heterozygosity at the p53 tumor suppressor locus have been correlated with various types of cancer. Ridanpaa et al., *Path. Res. Pract.*, 191: 399–402 (1995); Hollstein et al., *Science*, 253: 49–53 (1991). In addition, the loss or other mutation of the apc and dcc tumor suppressor genes has also been associated with tumor development. Blum, *Europ. J. Cancer*, 31A: 1369–1372 (1995). Those mutations can serve as markers for early stages of disease and for predisposition thereto. Early diagnosis is not only important for successful treatment, but can also lead to prevention or treatment before chronic symptoms occur.

Colorectal cancer is an example of a disease that is highly curable if detected early. With early detection, colon cancer may be effectively treated by, for example, surgical removal of the cancerous tissue. Surgical removal of early-stage colon cancer is usually successful because colon cancer begins in cells of the colonic epithelium and is isolated from the general circulation during its early stages. Thus, detection of early mutations in colorectal cells would greatly increase survival rate. Current methods for detection of colorectal cancer focus on extracellular indicia of the presence of cancer, such as the presence of fecal occult blood or carcinoembryonic antigen circulating in serum. Such extracellular indicia typically occurs only after the cancer has become invasive. At that point, colorectal cancer is very difficult to treat.

Methods have been devised to detect the presence of mutations within disease-associated genes. One such method is to compare the complete nucleotide sequence of a sample genomic region with the corresponding wild-type region. See, e.g., Engelke et al., *Proc. Natl. Acad. Sci, U.S.A.*, 85: 544–548 (1988); Wong et al., *Nature*, 330: 384–386 (1988). However, such methods are costly, time consuming, and require the analysis of multiple clones of the targeted gene for unambiguous detection of low-frequency mutations. As such, it is not practical to use extensive sequencing for large-scale screening of genetic mutations.

A variety of detection methods have been developed which exploit sequence variation in DNA using enzymatic and chemical cleavage techniques. A commonly-used screen for DNA polymorphisms consists of digesting DNA with restriction endonucleases and analyzing the resulting fragments by means of southern blots, as reported by Botstein et al., *Am. J. Hum. Genet.*, 32: 314–331 (1980) and White et al., *Sci. Am.*, 258: 40–48 (1988). Mutations that affect the recognition sequence of the endonuclease will preclude enzymatic cleavage at that site, thereby altering the cleavage pattern of the DNA. Sequences are compared by looking for differences in restriction fragment lengths. A problem with this method (known as restriction fragment length polymorphism mapping or RFLP mapping) is its inability to detect mutations that do not affect cleavage with a restriction endonuclease. One study reported that only 0.7% of the mutational variants estimated to be present in a 40,000 base pair region of human DNA were detected using RFLP analysis. Jeffreys, *Cell*, 18: 1–18 (1979).

Single base mutations have been detected by differential hybridization techniques using allele-specific oligonucleotide (ASO) probes. Saiki et al., *Proc. Natl. Acad. Sci. USA*, 86: 6230–6234 (1989). Mutations are identified on the basis of the higher thermal stability of the perfectly-matched probes as compared to mismatched probes. Disadvantages of this approach for mutation analysis include: (1) the requirement for optimization of hybridization for each probe, and (2) the nature of the mismatch and the local sequence impose limitations on the degree of discrimination of the probes. In practice, tests based only on parameters of nucleic acid hybridization function poorly when the sequence complexity of the test sample is high (e.g., in a heterogeneous biological sample). This is partly due to the small thermodynamic differences in hybrid stability generated by single nucleotide changes. Therefore, nucleic acid hybridization is generally combined with some other selection or enrichment procedure for analytical and diagnostic purposes.

In enzyme-mediated ligation methods, a mutation is interrogated by two oligonucleotides capable of annealing immediately adjacent to each other on a target DNA or RNA molecule, one of the oligonucleotides having its 3' end complementary to the point mutation. Adjacent oligonucleotide sequences are only covalently attached when both oligonucleotides are correctly base-paired. Thus, the presence of a point mutation is indicated by the ligation of the two adjacent oligonucleotides. Grossman et al., *Nucleic Acid Research*, 22: 4527–4534 (1994). However, the usefulness of this method for detection is compromised by high backgrounds which arise from tolerance of certain nucleotide mismatches or from non-template directed ligation reactions. Barringer et al., *Gene*, 89: 117–122 (1990).

A number of detection methods have been developed which are based on a template-dependent, primer extension reaction. These methods fall essentially into two categories: (1) methods using primers which span the region to be interrogated for the mutation, and (2) methods using primers which hybridizes proximally and upstream of the region to be interrogated for the mutation.

In the first category, Caskey and Gibbs [U.S. Pat. No. 5,578,458] report a method wherein single base mutations in target nucleic acids are detected by competitive oligonucleotide priming under hybridization conditions that favor the binding of the perfectly-matched primer as compared to one with a mismatch. Vary and Diamond [U.S. Pat. No. 4,851, 331] described a similar method wherein the 3' terminal nucleotide of the primer corresponds to the variant nucleotide of interest. Since mismatching of the primer and the template at the 3' terminal nucleotide of the primer inhibits elongation, significant differences in the amount of incorporation of a tracer nucleotide result under normal primer extension conditions.

It has long been known that primer-dependent DNA polymerases have, in general, a low replication error rate. This feature is essential for the prevention of genetic mistakes which would have detrimental effects on progeny. Methods in a second category exploit the high fidelity inherent in this enzymological reaction. Detection of mutations is based on primer extension and incorporation of detectable, chain-terminating nucleoside triphosphates. The high fidelity of DNA polymerases ensures specific incorporation of the correct base labeled with a reporter molecule. Such single nucleotide primer-guided extension assays have been used to detect aspartylglucosaminuria, hemophilia B, and cystic fibrosis; and for quantifying point mutations associated with Leber Hereditary Optic Neuropathy (LHON). See. e.g., Kuppuswamy et al., *Proc. Natl. Acad. Sci. USA*, 88: 1143–1147 (1991); Syvanen et al., *Genomics*, 8: 684–692 (1990); Juvonen et al., *Human Genetics*, 93: 16–20 (1994); Ikonen et al., *PCR Meth. Applications*, 1: 234–240 (1992); Ikonen et al., *Proc. Natl. Acad. Sci. USA*, 88: 11222–11226 (1991); Nikiforov et al., *Nucleic Acids Research*, 22: 4167–4175 (1994). An alternative primer extension method involving the addition of several nucleotides prior to the chain terminating nucleotide has also been proposed in order to enhance resolution of the extended primers based on their molecular weights. See e.g., Fahy et al., WO/96/30545 (1996).

Strategies based on primer extension require considerable optimization to ensure that only the perfectly annealed oligonucleotide functions as a primer for the extension reaction. The advantage conferred by the high fidelity of the polymerases can be compromised by the tolerance of nucleotide mismatches in the hybridization of the primer to the template. Any "false" priming will be difficult to distinguish from a true positive signal.

The selectivity and sensitivity of an oligonucleotide primer extension assay are related to the length of the oligonucleotide primer, and to the reaction conditions. In general, primer lengths and reaction conditions that favor high selectivity result in low sensitivity. Conversely, primer lengths and reaction conditions that favor high sensitivity result in low selectivity.

Under typical reaction conditions, short primers (i.e., less than about a 15-mer) exhibit transient, unstable hybridization. Therefore, the sensitivity of a primer extension assay is low when a short primer is used, because a transient, unstable oligonucleotide hybrid does not readily prime the extension reaction, resulting in a low yield of extended oligonucleotide. Moreover, in a complex heterogeneous biological sample, short primers exhibit non-specific binding to a wide variety of perfectly-matched complementary sequences. Thus, because of their low stability and high non-specific binding, short primers are not very useful for reliable identification of a mutation at a known location. Therefore, detection methods based on primer extension assays use oligonucleotide primers ranging in length from 15-mer to 25-mer. See e.g., PCT Patent Publications WO 91/13075; WO 92/15712; and WO 96/30545. Lengthening the probe to increase stability, however, has the effect of diminishing selectivity. A single base mismatch usually has less effect on the binding efficiency of a longer oligonucleotide primer than it does on that of a shorter primer, because of the relatively smaller thermodynamic difference between a mismatched primer and a perfectly matched primer. This higher tolerance of nucleotide mismatches in the hybridization of the longer primer to the template can result in higher levels of non-specific "false" priming in complex heterogeneous biological samples.

The reaction conditions of a primer extension reaction can be optimized to reduce "false" priming due to a mismatched oligonucleotide. However, optimization is labor intensive and expensive, and often results in lower sensitivity due to a reduced yield of extended primer. Moreover, since considerable optimization is required to ensure that only the perfectly annealed oligonucleotide functions as a primer for the extension reaction, only limited multiplexing of the primer extension assays is possible. Krook et al., supra report that multiplexing can be achieved by using primers of different lengths and by monitoring the wild-type and mutant nucleotide at each mutation site in two separate single nucleotide incorporation reactions. However, given that the selectivity and stability of the oligonucleotide primer extension assay is determined by the length of the oligonucleotide primer and the reaction conditions, the number of primers that can be tested simultaneously in a given reaction mixture is very limited.

Methods in the art reduce the possibility of false priming by decreasing the sequence complexity of the test sample. Thus, genomic DNA is isolated from the biological sample and/or amplified with PCR using primers which flank the region to be interrogated. The primer extension analysis is then conducted on the purified PCR products. See PCT Patent Publications WO 91/13075; WO 92/15712; and WO 96/30545. However, these methods are time consuming and expensive, because they involve additional steps of sample processing. Furthermore, these methods are not adapted for multiple primer extension reactions in a single sample.

Therefore, there is a need in the art for a selective and sensitive nucleic acid detection method, and for reliable large-scale screening methods for a large number of genomic mutations in heterogeneous biological samples. Such methods are provided herein.

SUMMARY OF THE INVENTION

The invention provides methods of mutation detection having high sensitivity and high selectivity. In a general embodiment, the invention comprises a single base extension reaction that is repeated at least once. Methods of the invention are useful to detect and identify genetic mutations or the presence of disease-causing microorganisms in an heterogeneous biological sample.

Methods of the invention comprise conducting multiple cycles of a single-base extension reaction, thereby increasing the sensitivity of the primer extension assay without compromising the selectivity. In a preferred embodiment, methods of the invention comprise between 2 and 100 cycles of primer extension. More preferably, between 10 and 50 cycles are performed. Most preferably, approximately 30 cycles are performed.

In a preferred embodiment, an excess of primer is used, to ensure that additional extended primer products are produced in each extension cycle. The oligonucleotide primer length is preferably between about 10 to about 100 nucleotides, more preferably between about 15 and about 35 nucleotides, and most preferably about 25 nucleotides.

In a preferred embodiment, each extension reaction includes conditions that promote hybridization of the primer only to nucleic acids with a perfect complementary sequence (i.e. mismatched base pairs are not tolerated). In one embodiment, the hybridization is performed at about the Tm for the primer in the assay. In a more preferred embodiment, the hybridization is performed above the Tm for the primer.

In one embodiment, a hybridized oligonucleotide primer is extended with a labeled terminal nucleotide. Labeled ddNTPs or dNTPs preferably comprise a "detection moiety" which facilitates detection of the extended primer. Detection moieties are selected from the group consisting of fluorescent, luminescent or radioactive labels, enzymes, haptens, and other chemical tags such as biotin which allow for easy detection of labeled extension products by, for example, spectrophotometric methods.

In a preferred embodiment, a further cycle of primer extension is started by denaturing the hybridized and extended primer, annealing nonextended primer, and extending the newly hybridized primer. The presence of excess primer in the reaction promotes annealing of nonextended primer in each cycle of the reaction.

In a further embodiment, methods of the invention comprise conducting at least two cycles of a single-base extension reaction using segmented primers. Methods of the invention comprise hybridizing two probes adjacent to a site of suspected mutation, wherein neither probe alone is capable of being a primer for template-dependent extension, but when the probes hybridize adjacent to each other, they are capable of priming extension. In a preferred embodiment, methods of the invention comprise hybridizing to a target nucleic acid a probe having a length from about 5 bases to about 10 bases, wherein the probe hybridizes immediately upstream of a suspected mutation. Methods of the invention further comprise hybridizing a second probe upstream of the first probe, the second probe having a length from about 15 to about 100 nucleotides and having a 3' non-extendible nucleotide. The second probe is substantially contiguous with the first probe. Preferably, substantially contiguous probes are between 0 and about 1 nucleotide apart. A linker is preferably used where the first and second probes are separated by two or more nucleotides, provided the linker does not interfere with the nucleic acid extension reaction. Such linkers are known in the art and include, for example, peptide nucleic acids, DNA binding proteins, and ligation.

In an alternative embodiment, segmented primers comprise a series of first oligonucleotide probes. No member of the series of the first probes is capable of being a primer for nucleic acid polymerization unless every member of said series hybridize simultaneously to substantially contiguous portions of the target nucleic acid, thereby forming a contiguous primer. In one embodiment, the segmented primers comprise three 8-mer first probes. In another embodiment, the segmented primers comprise four 6-mer first probes.

In each cycle of the extension assay, an extension reaction adds nucleotides to the segmented primer resulting from co-hybridization of the above-described probes in a template-dependent manner. In a preferred embodiment, first probes hybridized to a target nucleic acid are extended with a labeled terminal nucleotide whereas first probes hybridized to a wild-type or non-target nucleic acid are extended with an unlabeled terminal nucleotide. Labeled ddNTPs or dNTPs preferably comprise a "detection moiety" which facilitates detection of the short probes that have been extended with a labeled terminal nucleotide. Detection moieties are selected from the group consisting of fluorescent, luminescent or radioactive labels, enzymes, haptens, and other chemical tags such as biotin which allow for easy detection of labeled extension products by, for example, spectrophotometric methods.

In a preferred embodiment, several cycles of extension reactions are conducted in order to amplify the assay signal. Extension reactions are conducted in the presence of an excess of first and second probes, labeled dNTPs or ddNTPs, and heat-stable polymerase. Once an extension reaction is completed, the first and second probes bound to target nucleic acids are dissociated by heating the reaction mixture above the melting temperature of the hybrids. The reaction mixture is then cooled below the melting temperature of the hybrids and first and second probes are permitted to associate with target nucleic acids for another extension reaction. In a preferred embodiment, 10 to 50 cycles of extension reactions are conducted. In a most preferred embodiment, 30 cycles of extension reactions are conducted.

Methods disclosed herein may be used to detect single nucleotide polymorphisms (SNPs), mutations such as insertions, deletions, and substitutions. Nucleic acid samples that can be screened with the methods of the present invention include human nucleic acid samples. A primer (or segmented primer) is designed so that the 3' end of the hybridized primer is immediately upstream of the position that is complementary to the nucleotide position being assayed. The nucleotide position being assayed is identified as the nucleotide that is complementary to the nucleotide incorporated in the single-base primer extension reaction. For example, if a G is incorporated in the reaction, a C is present at the complementary position on the nucleic acid in the biological sample. In a preferred embodiment, a primer extension reaction is performed in the presence of four nucleotides, preferably chain terminating nucleotides, for example the dideoxynucleotides ddATP, ddCTP, ddGTP, and ddTTP. In a more preferred embodiment, the nucleotides are detectably labeled, preferably differentially labeled. In alternative embodiments, the extension reaction is performed in the presence of one, two, or three different nucleotides. If the biological sample is heterogeneous at the nucleotide position being assayed, the complementary nucleotides (if they are included in the primer extension reaction) will be incorporated in the primer extension assay.

Methods disclosed herein may be used to detect mutations associated with diseases such as cancer. Additionally, methods of the invention may be used to detect a deletion or a base substitution mutation causative of a metabolic error, such as complete or partial loss of enzyme activity.

In another embodiment, the specific nucleic acid sequence comprises a portion of a particular gene or genetic locus in the patient's genomic nucleic acid known to be involved in a pathological condition or syndrome. Non-limiting examples include cystic fibrosis, Tay-Sachs disease, sickle-cell anemia, β-thalassemia, and Gaucher's disease.

In yet another embodiment, the specific nucleic acid sequence comprises part of a particular gene or genetic locus that may not be known to be linked to a particular disease, but in which polymorphism is known or suspected.

In yet another embodiment, the specific nucleic acid sequence comprises part of a foreign genetic sequence e.g. the genome of an invading microorganism. Non-limited examples include bacteria and their phages, viruses, fungi, protozoa, and the like. The present methods are particularly applicable when it is desired to distinguish between different variants or strains of a microorganism in order to choose appropriate therapeutic interventions.

Genomic nucleic acid samples are isolated from a biological sample. Once isolated, the nucleic acids may be employed in the present invention without further manipulation. Alternatively, one or more specific regions present in the nucleic acids may be amplified by, for example, PCR. Amplification at this step provides the advantage of increasing the concentration of specific nucleic acid sequences within the target nucleic acid sequence population. In another embodiment, genomic nucleic acids are fragmented before further analysis.

In one embodiment, the nucleic acids are bound to a solid-phase support. This allows the simultaneous processing and screening of a large number of samples. Non-limiting examples of supports suitable for use in the present invention include nitrocellulose or nylon filters, glass beads, magnetic beads coated with agents for affinity capture, treated or untreated microtiter plates, and the like. In a preferred embodiment, the support is a microtiter dish, having a multiplicity of wells. The use of such a support allows the simultaneous determination of a large number of samples and controls, and thus facilitates the analysis. Moreover, automated systems can be used to provide reagents to such microtiter dishes. In an alternative embodiment, methods of the invention are conducted in an aqueous phase.

In one embodiment of the invention, the extended primers or probes are enumerated. The primers or probes are preferably extended with a nucleotide labeled with an impedence bead, and the number of impedence beads is counted (using for example a Coulter counter). The number of labeled primers is then determined from the number of impedence beads. The label is more preferably a radioactive isotope, and the amount of radioactive decay associated with the labeled primer or probe is determined. The number of labeled primers or probes is calculated from the amount of radioactive decay. The numbers of extended primers or probes are useful for a statistical analysis of the cycled extension reaction.

Finally, methods of the invention further comprise isolating and sequencing the extended primers or first probes. Primers or first probes preferably comprise a "separation moiety" that facilitates their isolation. Non-limiting examples of separation moieties include hapten, biotin, and digoxigenin. In a preferred embodiment, primers or first probes comprising a separation moiety are immobilized to a solid support having affinity for the separation moiety (e.g., coated with anti-hapten, avidin, streptavidin, or anti-digoxigenin). The solid support is selected from the group consisting of glass, plastic, and paper. The support is fashioned as a column, bead, dipstick, or test tube. In a preferred embodiment, the separation moiety is incorporated in the labeled ddNTPs or dNTPs and only first probes extended with a labeled ddNTP or dNTP are immobilized to the support. As such, labeled primers or first probes are isolated from unextended primers or first probes and second probes. In an alternative preferred embodiment, the separation moiety is incorporated in all the first probes, provided the separation moiety does not interfere with the first probe's ability to hybridize with template and to be extended. By incorporating the separation moiety in the first probes, all first probes are immobilized to a solid support. First probes are isolated from second probes by one or more washing steps.

Labeled primers or first probes are then sequenced to identify a mutation or disease-causing microorganism. In one embodiment, the immobilized primers or probes are directly subjected to sequencing, using for example, chemical methods standard in the art. In other embodiments, the labeled first probes are removed from the solid support and sequencing of labeled first probes is performed in aqueous solution. The isolated first probes are contacted with a multiplicity of complementary oligonucleotides. In one embodiment, enzymatic sequencing is performed using the isolated first probes as primers and the complementary oligonucleotides as templates. In an alternative embodiment, a single base extension reaction is performed using the isolated first probes as primers and the complementary oligonucleotides as templates. The sequence of the extension product is determined by enzymatic sequencing. The sequence of the extended labeled first probes identifies the genetic mutations or the disease-causing microorganisms present in the sample.

Further aspects and advantages of the invention are apparent upon consideration of the following detailed description thereof.

DETAILED DESCRIPTION OF THE INVENTION

Figure 1:
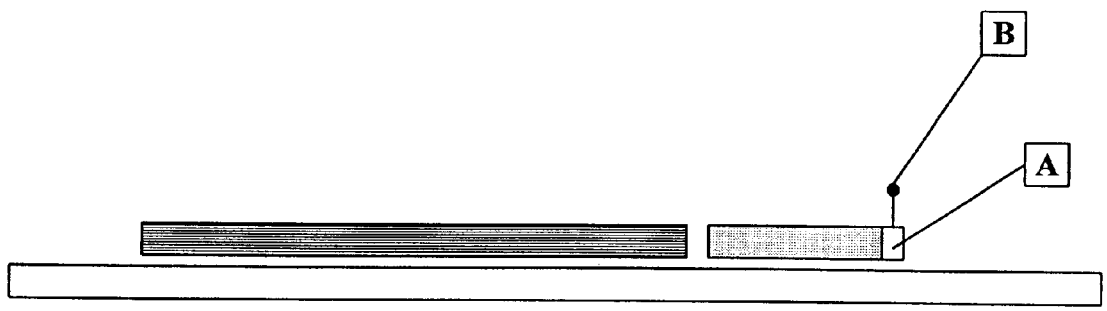
FIG. 1 is a diagram depicting the use of a segmented primer in a single base extension reaction for the detection of single base polymorphisms. The white bar represents the template, the dark gray bar represents second probe which hybridizes to a region on the template that is substantially contiguous with the first probe (light gray). The site suspected to be a single base mutation is labeled A. The detectable label is marked B.

The present invention is the first to provide a single base extension assay with both high selectivity and high sensitivity. The present invention provides methods for detecting specific nucleic acids in a biological sample with both high sensitivity and high selectivity. The present methods provide the high selectivity of stringent hybridization condition, without losing sensitivity due to low yield of extended product. In general, methods of the invention comprise performing multiple cycles of a single base extension reaction in a biological sample. By cycling, extended product yield is high, and there is no significant loss of selectivity because hybridization conditions for the primer are kept stringent relative to those typically applied during a single-base extension reaction. Methods of the invention are useful to detect and identify mutations associated with diseases such as cancer, deletions or a base substitution mutations causative of a metabolic error, such as complete or partial loss of enzyme activity, portions of a particular gene or genetic locus in the patient's genomic nucleic acid known to be involved in a pathological condition or syndrome, single nucleotide polymorphisms (SNPs), or part of a foreign genetic sequence e.g. the genome of an invading disease-causing microorganism.

A single base primer extension reaction is performed by annealing an oligonucleotide primer to a complementary nucleic acid, and by extending the 3' end of the annealed primer with a chain terminating nucleotide that is added in a template directed reaction catalyzed by a DNA polymerase. The selectivity and sensitivity of a single base primer extension reaction are affected by the length of the oligonucleotide primer and the reaction conditions (e.g. annealing temperature, salt concentration).

The selectivity of a primer extension reaction reflects the amount of exact complementary hybridization between an oligonucleotide primer and a nucleic acid in a sample. A highly selective reaction promotes primer hybridization only to nucleic acids with an exact complementary sequence (i.e. there are no base mismatches between the hybridized primer and nucleic acid). In contrast, in a non selective reaction, the primer also hybridizes to nucleic acids with a partial complementary sequence (i.e. there are base mismatches between the hybridized primer and nucleic acid). In general, parameters which favor selective primer hybridization (for example shorter primers and higher annealing temperatures) result in a lower level of hybridized primer. Therefore, parameters which favor a selective single-base primer extension assay result in decreased sensitivity of the assay.

Methods of the invention comprise conducting at least two cycles of a single-base extension reaction. By repeating the single-base extension reaction, methods of the invention increase the signal of a single-base primer extension assay, without reducing the selectivity of the assay. The cycling increases the signal, and the extension reaction can therefore be performed under highly selective conditions (for example, the primer is annealed at about or above its Tm).

In a preferred embodiment, methods of the invention are performed by annealing an excess of primer under conditions which favor exact hybridization, extending the hybridized primer, denaturing the extended primer, and repeating the annealing and extension reactions at least once. In a most preferred embodiment, the reaction cycle comprises a step of heat denaturation, and the polymerase is temperature stable (for example, Taq polymerase or Vent polymerase).

Preferred primer lengths are between 10 and 100 nucleotides, more preferably between 10 and 50 nucleotides, and most preferably about 30 nucleotides. Useful primers are those that hybridize adjacent a suspected mutation site, such that a single base extension at the 3' end of the primer incorporates a nucleotide complementary to the mutant nucleotide if it is present on the template.

Preferred hybridization conditions comprise annealing temperatures about or above the Tm of the oligonucleotide primer in the reaction. The Tm of an oligonucleotide primer is determined by its length and GC content, and is calculated using one of a number of formulas known in the art. Under standard annealing conditions, a preferred formula for a primer approximately 25 nucleotides long, is Tm (° C.)=4×(Number of Gs+Number of Cs)+2×(Number of As+Number of Ts).

In a preferred reaction, the annealing and denaturation steps are performed by changing the reaction temperature. In one embodiment of the invention, the primer is annealed at about the Tm for the primer, the temperature is raised to the optimal temperature for extension, the temperature is then raised to a denaturing temperature. An example of annealing, extension and denaturing temperatures and times is described in Example 2. In a more preferred embodiment of the invention, the reaction is cycled between the annealing temperature and the denaturing temperature, and the single base extension occurs during transition from annealing to denaturing conditions.

In a preferred embodiment of the invention, two or more cycles of extension are performed. In a more preferred embodiment, between 5 and 100 cycles are performed. In a further embodiment, between 10 and 50 cycles, and most preferably about 30 cycles are performed.

In a preferred embodiment of the invention, the nucleotide added to the 3' end of the primer in a template dependent reaction is a chain terminating nucleotide, for example a dideoxynucleotide. In a more preferred embodiment, the nucleotide is detectably labeled as discussed infra.

I. CYCLED EXTENSION REACTIONS WITH SEGMENTED PRIMERS

In one embodiment, methods of the invention comprise conducting at least two cycles of single-base extension with a segmented primer. In a preferred embodiment, the segmented primer comprises a short first probe and a longer second probe capable of hybridizing to substantially contiguous portions of the target nucleic acid. The two probes are exposed to a sample under conditions that do not favor the hybridization of short first probe in the absence of longer second probe. Factors affecting hybridization are well known in the art and include temperature, ion concentration, pH, probe length, and probe GC content. A first probe, because of its small size, hybridizes numerous places in an average genome. For example, any given 8-mer occurs about 65,000 times in the human genome. However, an 8-mer has a low melting temperature ($T_m$) and a single base mismatch greatly exaggerates this instability. A second probe, on the other hand, is larger than the first probe and will have a higher $T_m$. A 20-mer second probe, for example, typically hybridizes with more stability than an 8-mer. However, because of the small thermodynamic differences in hybrid stability generated by single nucleotide changes, a longer probe will form a stable hybrid but will have a lower selectivity because it will tolerate nucleotide mismatches. Accordingly, under unfavorable hybridization conditions for the first probe (e.g., 10–40° C. above first probe $T_m$), the first probe hybridizes with high selectivity (i.e., hybridizes poorly to sequence with even a single mismatch), but forms unstable hybrids when it hybridizes alone (i.e., not in the presence of a second probe). The second probe will form a stable hybrid but will have a lower selectivity because of its tolerance of mismatches.

The extension reaction in the present invention will not occur absent contiguous hybridization of the first and second probes. A first (proximal) probe alone is not a primer for template-based nucleic acid extension because it will not form a stable hybrid under the reaction conditions used in the assay. Preferably, the first probe comprises between about 5 and about 10 nucleotides. The first probe hybridizes adjacent to a nucleic acid suspected to be mutated. A second (distal) probe in mutation identification methods of the invention hybridizes upstream of the first probe and to a substantially contiguous region of the target (template). The second probe alone is not a primer of template-based nucleic acid extension because it comprises a 3' non-extendible nucleotide. The second probe is larger than the first probe, and is preferably between about 15 and about 100 nucleotides in length.

According to methods of the invention, template-dependent extension takes place only when a first probe hybridizes next to a second probe. When this happens, the short first probe hybridizes immediately adjacent to the site of the suspected single base mutation. The second probe hybridizes in close proximity to the 5' end of the first probe. The presence of the two probes together increases stability due to cooperative binding effects. Together, the two probes are recognized by polymerase as a primer. This system takes advantage of the high selectivity of a short probe and the hybridization stability imparted by a longer probe in order to generate a primer that hybridizes with the selectivity of a short probe and the stability of a long probe. Accordingly, there is essentially no false priming with segmented primers. Since the tolerance of mismatches by the longer second probe will not generate false signals, several segmented primers can be assayed in the same reaction, as long as the hybridization conditions do not permit the extension of short first probes in the absence of the corresponding longer second probes. Moreover, due to their increased selectivity for target, methods of the invention may be used to detect and identify a target nucleic acid that is available in small proportion in a sample and that would normally have to be amplified by, for example, PCR in order to be detected.

By requiring hybridization of the two probes, false positive signals are reduced or eliminated. As such, the use of segmented oligonucleotides eliminates the need for careful optimization of hybridization conditions for individual probes, as presently required in the art, and permits extensive multiplexing. Several segmented oligonucleotides can be used to probe several target sequences assayed in the same reaction, as long as the hybridization conditions do not permit stable hybridization of short first probes in the absence of the corresponding longer second probes.

The first and second probes hybridize to substantially contiguous portions of the target. For purposes of the present invention, substantially contiguous portions are those that are close enough together to allow hybridized first and second probes to function as a single probe (e.g., as a primer of nucleic acid extension). Substantially contiguous portions are preferably between zero (i.e., exactly contiguous so there is no space between the portions) nucleotides and about one nucleotide apart. A linker is preferably used where the first and second probes are separated by two or more nucleotides, provided the linker does not interfere with the assay (e.g., nucleic acid extension reaction). Such linkers are known in the art and include, for example, peptide nucleic acids, DNA binding proteins, and ligation. It has now been realized that the adjacent probes bind cooperatively so that the longer, second probe imparts stability on the shorter, first probe. However, the stability imparted by the second probe does not overcome the selectivity (i.e., intolerance of mismatches) of the first probe. Therefore, methods of the invention take advantage of the high selectivity of the short first probe and the hybridization stability imparted by the longer second probe.

Thus, in a preferred embodiment, first and second probes are hybridized to substantially contiguous regions of target, wherein the first probe is immediately adjacent and upstream of a site of suspected mutation, for example, a single base mutation. The sample is then exposed to dideoxy nucleic acids that are complements of possible mutations at the suspected site. For example, if the wild-type nucleic acid at a known site is adenine, then dideoxy adenine, dideoxy cytosine, and dideoxy guanine are placed into the sample. Preferably, the dideoxy nucleic acids are labeled. Deoxynucleotides may alternatively be used if the reaction is stopped after the addition of a single nucleotide. Polymerase, either endogenously or exogenously supplied, catalyzes incorporation of a dideoxy base on the first probe. Detection of label indicates that a non-wild-type (i.e., mutant) base has been incorporated, and there is a mutation at the site adjacent the first probe. Alternatively, methods of the invention may be practiced when the wild-type sequence is unknown. In that case, the four common dideoxy nucleotides are differentially labeled. Appearance of more than one label in the assay described above indicates a mutation may exist.

In an alternative preferred embodiment, a segmented oligonucleotide comprises a series of first probes, wherein sufficient stability is only obtained when all members of the segmented oligonucleotide simultaneously hybridize to substantially contiguous portions of a nucleic acid. It has now been realized that, although short probes exhibit transient, unstable hybridization, adjacent short probes bind cooperatively and with greater stability than each individual probe. Together, a series of adjacently-hybridized first probes will have greater stability than individual probes or a subset of probes in the series. For example, in an extension reaction with a segmented primer comprising a series of three first probes (i.e., three short probes with no terminal nucleotide capable of hybridizing to a substantially contiguous portion of a nucleic acid upstream of the target nucleic acid), the concurrent hybridization of the three probes will generate sufficient cooperative stability for the three probes to prime nucleic acid extension and the short probe immediately adjacent to a suspected mutation will be extended. Thus, segmented probes comprising a series of short first probes offer the high selectivity (i.e., intolerance of mismatches) of short probes and the stability of longer probes.

In a preferred embodiment, several cycles of extension reactions are conducted in order to amplify the assay signal. Extension reactions are conducted in the presence of an excess of first and second probes, labeled dNTPs or ddNTPs, and heat-stable polymerase. Once an extension reaction is completed, the first and second probes bound to target nucleic acids are dissociated by heating the reaction mixture above the melting temperature of the hybrids. The reaction mixture is then cooled below the melting temperature of the hybrids and first and second probes permitted to associate with target nucleic acids for another extension reaction. In a preferred embodiment, 10 to 50 cycles of extension reactions are conducted. In a most preferred embodiment, 30 cycles of extension reactions are conducted.

II. DETECTION OF EXTENDED PRIMERS

Labeled ddNTPs or dNTPs preferably comprise a "detection moiety" which facilitates detection of the extended primers, or extended short first probes in a segmented primer reaction. Detection moieties are selected from the group consisting of fluorescent, luminescent or radioactive labels, enzymes, haptens, and other chemical tags such as biotin which allow for easy detection of labeled extension products. Fluorescent labels such as the dansyl group, fluorescein and substituted fluorescein derivatives, acridine derivatives, coumarin derivatives, pthalocyanines, tetramethylrhodamine, Texas Red®, 9-(carboxyethyl)-3-hydroxy-6-oxo-6H-xanthenes, DABCYL® and BODIPY® (Molecular Probes, Eugene, Oreg.), for example, are particularly advantageous for the methods described herein. Such labels are routinely used with automated instrumentation for simultaneous high throughput analysis of multiple samples.

In a preferred embodiment, primers or first probes comprise a "separation moiety." Such separation moiety is, for example, hapten, biotin, or digoxigenin. These primers or first probes, comprising a separation moiety, are isolated from the reaction mixture by immobilization on a solid-phase matrix having affinity for the separation moiety (e.g., coated with anti-hapten, avidin, streptavidin, or anti-digoxigenin). Non-limiting examples of matrices suitable for use in the present invention include nitrocellulose or nylon filters, glass beads, magnetic beads coated with agents for affinity capture, treated or untreated microtiter plates, and the like.

In a preferred embodiment, the separation moiety is incorporated in the labeled ddNTPs or dNTPs. By denaturing hybridized primers or probes, and immobilizing primers or first probes extended with a labeled ddNTP or dNTP to a solid matrix, labeled primers or labeled first probes are isolated from unextended primers or unextended first probes and second probes, and primers or first probes extended with an unlabeled ddNTPs by one or more washing steps.

In an alternative preferred embodiment, the separation moiety is incorporated in the primers or first probes, provided the separation moiety does not interfere with the first primer's or probe's ability to hybridize with template and be extended. Eluted primers or first probes are immobilized to a solid support and can be isolated from eluted second probes by one or more washing steps.

Alternatively, the presence of primers or first probes that have been extended with a labeled terminal nucleotide may be determined without eluting hybridized primers or probes. The methods for detection will depend upon the label or tag incorporated into the primers or first probes. For example, radioactively labeled or chemiluminescent first probes that have bound to the target nucleic acid can be detected by exposure of the filter to X-ray film. Alternatively, primers or first probes containing a fluorescent label can be detected by excitation with a laser or lamp-based system at the specific absorption wavelength of the fluorescent reporter.

In an alternative embodiment, the bound primers or first and second probes are eluted from a matrix-bound target nucleic acid (see below). Elution may be accomplished by any means known in the art that destabilizes nucleic acid hybrids (i.e., lowering salt, raising temperature, exposure to formamide, alkali, etc.). In a preferred embodiment, the bound oligonucleotide probes are eluted by incubating the target nucleic acid-segmented primer complexes in water, and heating the reaction above the melting temperature of the hybrids.

Deoxynucleotides may be used as the detectable single extended base in any of the reactions described above that require single base extension. However, in such methods, the extension reaction must be stopped after addition of the single deoxynucleotide. Such methods may be employed regardless of whether a specific mutation is known (i.e., C→G). Moreover, the extension reaction need not be terminated after the addition of only one deoxynucleotide if only one labeled species of deoxynucleotide is made available in the sample for detection of the single base mutation. This method may actually enhance signal if there is a nucleotide repeat including the interrogated single base position.

In a preferred embodiment, target nucleic acids are immobilized to a solid support prior to exposing the target nucleic acids to primers or segmented primers and conducting an extension reaction. Once the nucleic acid samples are immobilized, the samples are washed to remove non-immobilized materials. The nucleic acid samples are then exposed to one or more set of primers or segmented primers according to the invention. Once the single-base extension reaction is completed, the primers or first probes extended with a labeled ddNTP or dNTP are preferably isolated from unextended probes and probes extended with an unlabeled ddNTPs or dNTP. Bound primers or first and second probes are eluted from the support-bound target nucleic acid. Elution may be accomplished by any means known in the art that destabilizes nucleic acid hybrids (i.e., lowering salt, raising temperature, exposure to formamide, alkali, etc.). In a preferred embodiment, the first and second probes bound to target nucleic acids are dissociated by incubating the target nucleic acid-segmented primer complexes in water, and heating the reaction above the melting temperature of the hybrids and the extended first probes are isolated. In an alternative preferred embodiment, the extension reaction is conducted in an aqueous solution. Once the single-base extension reaction is completed, the oligonucleotide probes are dissociated from target nucleic acids and the extended first probes are isolated. In an alternative embodiment, the nucleic acids remain in aqueous phase.

Finally, methods of the invention comprise isolating and sequencing the extended first probes. A "separation moiety" such as, for example, hapten, biotin, or digoxigenin is used for the isolation of extended first probes. In a preferred embodiment, first probes comprising a separation moiety are immobilized to a solid support having affinity for the separation moiety (e.g., coated with anti-hapten, avidin, streptavidin, or anti-digoxigenin). Non-limiting examples of supports suitable for use in the present invention include nitrocellulose or nylon filters, glass beads, magnetic beads coated with agents for affinity capture, treated or untreated microtiter plates, and the like.

In a preferred embodiment, the separation moiety is incorporated in the labeled ddNTPs or dNTPs. By immobilizing eluted primers or first probes extended with a labeled ddNTP or dNTP to a solid support, labeled primers or first probes are isolated from unextended first probes and second probes, and primers or first probes extended with an unlabeled ddNTPs by one or more washing steps.

In an alternative preferred embodiment, the separation moiety is incorporated in the primers or first probes, provided the separation moiety does not interfere with the first primer's or probe's ability to hybridize with template and to be extended. Eluted primers or first probes are immobilized to a solid support and can be isolated from eluted second probes by one or more washing steps.

The labeled primers or first probes are then sequenced to identify the detected mutation or disease-causing microorganism. In one embodiment, the immobilized probes are directly subjected to sequencing, using a chemical method standard in the art. In other embodiments, the immobilized labeled first probes are removed from the solid support and sequencing of labeled first probes is performed in aqueous solution.

III. ENUMERATIVE DETECTION METHODS

Methods of the invention are useful in any context in which enumeration of nucleic acids is necessary or desirable. Primarily, detection methods discussed above are useful for detecting nucleotide mutations in biological samples. Accordingly, methods of the invention are useful for enumeration of a nucleic acid (e.g., an allele, a single nucleotide polymorphism or a mutation) associated, or suspected to be associated, with a disease. Once a number of a target nucleic acid has been determined in a patient sample, that number is compared to the number expected to be present if the sample were obtained from a healthy individual. A statistically-significant difference exists between the number of a nucleic acid in the patient sample and the number expected in a healthy patient (which number may be determined from pooled samples of healthy individuals), the patient is diagnosed as having a disease or the propensity therefor. Methods of the invention are also useful for detecting nucleic acids in biological samples, which are often heterogeneous, and mutated nucleic acids are often present in small amounts relative to wild-type nucleic acids. In stool samples for example, mutant nucleic acids from transformed cells shed onto the stool are rare relative to wild-type nucleic acids from normal cells shed onto the stool, especially in the early stages of colorectal cancer. Methods of the invention comprise statistical analysis to determine whether the results from a single-base extension assay of the invention are indicative of the presence of mutant nucleic acid in a biological sample. In a preferred embodiment, methods of the invention comprise enumeration of the single-base extended primers or probes. In a more preferred embodiment, the number of extended primers or probes is analyzed to determine whether a statistically significant amount of mutant nucleic acid sequence is present in the biological sample.

In one embodiment of the invention, primers or probes are preferably extended, as discussed herein, with a labeled nucleotide. The number of labeled primers is then determined. The label is more preferably a radioactive isotope, and the amount of radioactive decay associated with the labeled primer or probe is determined. The number of labeled primers or probes is calculated from the amount of radioactive decay. The number of molecules is counted by measuring a number X of radioactive decay events (e.g. by measuring the total number of counts during a defined interval or by measuring the time it takes to obtain a predetermined number of counts) specifically associated with the labeled primer or probe. The number X is used to calculate the number X1 of radionucleotides which are specifically associated with the labeled primer or probe. The number X1 is used to calculate the number X2 of labeled primer or probe molecules, knowing the number of radionucleotide molecules associated with each labeled molecule in the assay, as disclosed in co-owned, co-pending patent application Ser. No. 08/876,857 now U.S. Pat. No. 5,928, 870, incorporated by reference herein. The numbers of extended primers or probes present in the assay are useful for subsequent statistical analysis.

Methods of the present invention are useful for detecting loss of heterozygosity in a small number of cells in an impure cellular population, because such methods do not rely upon knowing the precise deletion end-points and such methods are not affected by the presence in the sample of heterogeneous DNA. For example, in loss of heterozygosity, deletions occur over large portions of the genome and entire chromosome arms may be missing. Methods of the invention comprise counting a number of molecules of a target nucleic acid suspected of being deleted and comparing it to a reference number. In a preferred embodiment the reference number is the number of molecules of a nucleic acid suspected of not being deleted in the same sample. All that one needs to know is at least a portion of the sequence of a target nucleic acid suspected of being deleted and at least a portion of the sequence of a reference nucleic acid suspected of not being deleted. Methods of the invention, while amenable to multiple mutation detection, do not require multiple mutation detection in order to detect indicia of cancer in a heterogeneous sample.

Accordingly, methods of the present invention are useful for the detection of loss of heterozygosity in a subpopulation of cells or debris therefrom in a sample. Loss of heterozygosity generally occurs as a deletion of at least one wild-type allelic sequence in a subpopulation of cells. In the case of a tumor suppressor gene, the deletion typically takes the form of a massive deletion characteristic of loss of heterozygosity. Often, as in the case of certain forms of cancer, disease-causing deletions initially occur in a single cell which then produces a small subpopulation of mutant cells. By the time clinical manifestations of the mutation are detected, the disease may have progressed to an incurable stage. Methods of the invention allow detection of a deletion when it exists as only a small percentage of the total cells or cellular debris in a sample.

Methods of the invention comprise a comparison of the number of molecules of two nucleic acids that are expected to be present in the sample in equal numbers in normal (non-mutated) cells. In a preferred embodiment, the comparison is between (1) an amount of a genomic polynucleotide segment that is known or suspected not to be mutated in cells of the sample (the "reference") and (2) an amount of a wild-type (non-mutated) genomic polynucleotide segment suspected of being mutated in a subpopulation of cells in the sample (the "target"). A statistically-significant difference between the amounts of the two genomic polynucleotide segments indicates that a mutation has occurred.

In a preferred embodiment, the reference and target nucleic acids are alleles of the same genetic locus. Alleles are useful in methods of the invention if there is a sequence difference which distinguishes one allele from the other. In a preferred embodiment, the genetic locus is on or near a tumor suppressor gene. Loss of heterozygosity can result in loss of either allele, therefore either allele can serve as the reference allele. The important information is the presence or absence of a statistically significant difference between the number of molecules of each allele in the sample. Also in a preferred embodiment, the reference and target nucleic acids are different genetic loci, for example different genes. In a preferred embodiment, the reference nucleic acid comprises both alleles of a reference genetic locus and the target nucleic acid comprises both alleles of a target genetic locus, for example a tumor suppressor gene. Specifically, in the case of a deletion in a tumor suppressor gene, the detected amount of the reference gene is significantly greater than the detected amount of the target gene. If a target sequence is amplified, as in the case of certain oncogene mutations, the detected amount of target is greater than the detected amount of the reference gene by a statistically-significant margin.

Methods according to the art generally require the use of numerous probes, usually in the form of PCR primers and/or hybridization probes, in order to detect a deletion or a point mutation. However, because methods of the present invention involve enumerative detection of nucleotide sequences and enumerative comparisons between sequences that are known to be stable and those that are suspected of being unstable, only a few probes must be used in order to accurately assess cancer risk. In fact, a single set (pair) of primers or probes is all that is necessary to detect a single large deletion. The risk of cancer is indicated by the presence of a mutation in a genetic region known or suspected to be involved in oncogenesis. Patients who are identified as being at risk based upon tests conducted according to methods of the invention are then directed to other, typically invasive, procedures for confirmation and/or treatment of the disease.

According to methods of the invention, the target and reference nucleic acids are differentially labeled using cycled single-base extension reactions that incorporate differently labeled nucleotides at the 3' ends of the primers or probes that selectively hybridize to the target and reference nucleic acids. For example, the primers or probes are designed such that template directed single-base extension of the primer or probe hybridized to the target nucleic acid results in addition of a T, whereas template directed single-base extension of the primer or probe hybridized to the reference nucleic acid results in addition of a G. The extension reactions are performed, for example, in the presence of $^{35}$S-labeled chain terminating T, and $^{32}$P-labeled chain terminating G. Alternatively, the two chain terminating nucleotides are labeled with large and small impedence beads, respectively. These chain terminating nucleotides can be labeled with any detectably different markers that allow enumeration of the extended primers or probes, as discussed herein.

Enumerative sampling of a nucleotide sequence that is uniformly distributed in a biological sample typically follows a Poisson distribution. For large populations, such as the typical number of genomic polynucleotide segments in a biological sample, the Poisson distribution is similar to a normal (Gaussian) curve with a mean, N, and a standard deviation that may be approximated as the square root of N.

Statistically-significance between numbers of target and reference genes obtained from a biological sample may be determined by any appropriate method. See, e.g., Steel, et al., Principles and Procedures of Statistics, A Biometrical Approach (McGraw-Hill, 1980), the disclosure of which is incorporated by reference herein. An exemplary method is to determine, based upon a desired level of specificity (tolerance of false positives) and sensitivity (tolerance of false negatives) and within a selected level of confidence, the difference between numbers of target and reference genes that must be obtained in order to reach a chosen level of statistical significance. A threshold issue in such a determination is the minimum number, N, of genes (for each of target and reference) that must be available in a population in order to allow a determination of statistical significance. The number N will depend upon the assumption of a minimum number of mutant alleles in a sample containing mutant alleles (assumed herein to be at least 1%) and the further assumption that normal samples contain no mutant alleles. It is also assumed that a threshold differences between the numbers of reference and target genes must be at least 0.5% for a diagnosis that there is a mutation present in a subpopulation of cells in the sample. Based upon the foregoing assumptions, it is possible to determine how large N must be so that a detected difference between numbers of mutant and reference alleles of less than 0.5% is truly a negative (i.e. no mutant subpopulation in the sample) result 99.9% of the time.

Figure 2A:
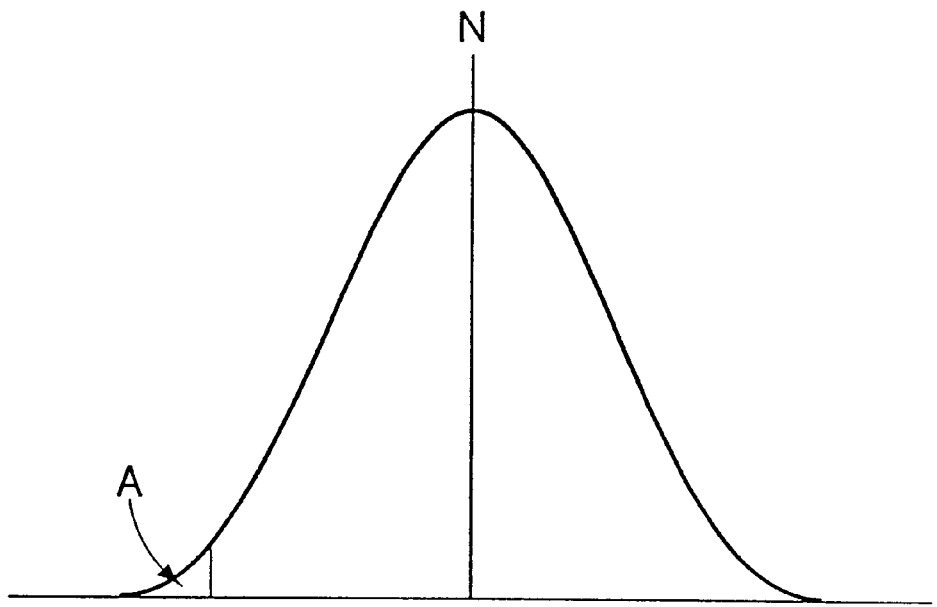
FIGS. 2A and 2B are model Gaussian distributions showing regions of low statistical probability.
Figure 2B:
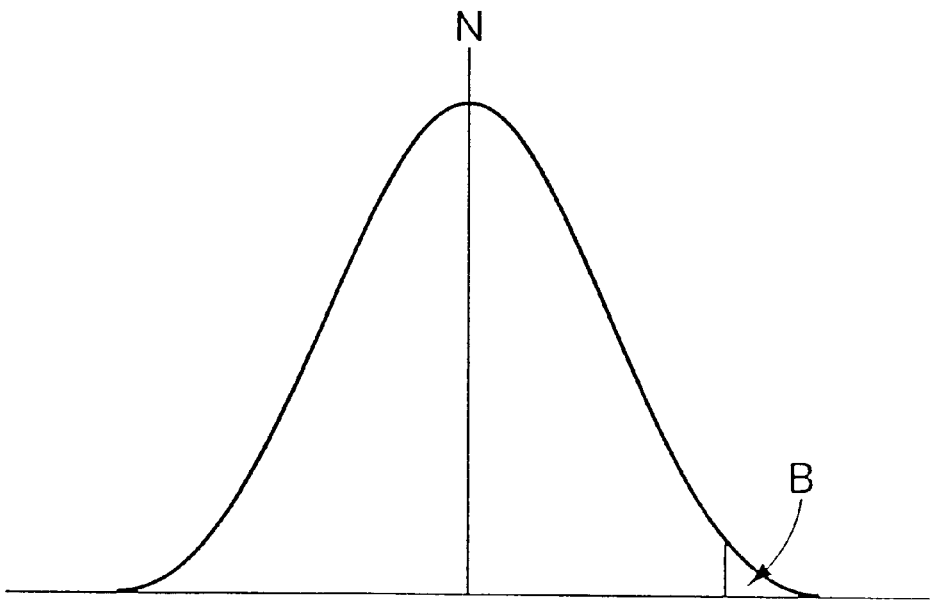

The calculation of N for specificity, then, is based upon the probability of one sample measurement being in the portion of the Gaussian distribution covering the lowest 3.16% of the population (the area marked "A" in FIG. 2A) and the probability that the other sample measurement is in the portion of the Gaussian distribution covering the highest 3.16% of the population (the area marked "B" in FIG. 2B). Since the two sample measurements are independent events, the probability of both events occurring simultaneously in a single sample is approximately 0.001 or 0.1%. Thus, 93.68% of the Gaussian distribution (100%−2×3.16%) lies between the areas marked A and B in FIG. 3. Statistical tables indicate that such area is equivalent to 3.72 standard deviations. Accordingly, 0.5% N is set equal to 3.72 sigma. Since sigma (the standard deviation) is equal to $\sqrt{N}$, the equation may be solved for N as 553,536. This means that if the lower of the two numbers representing reference and target is at least 553,536 and if the patient is truly normal, the difference between the numbers will be less than 0.5% about 99.9% of the time.

Figure 3:
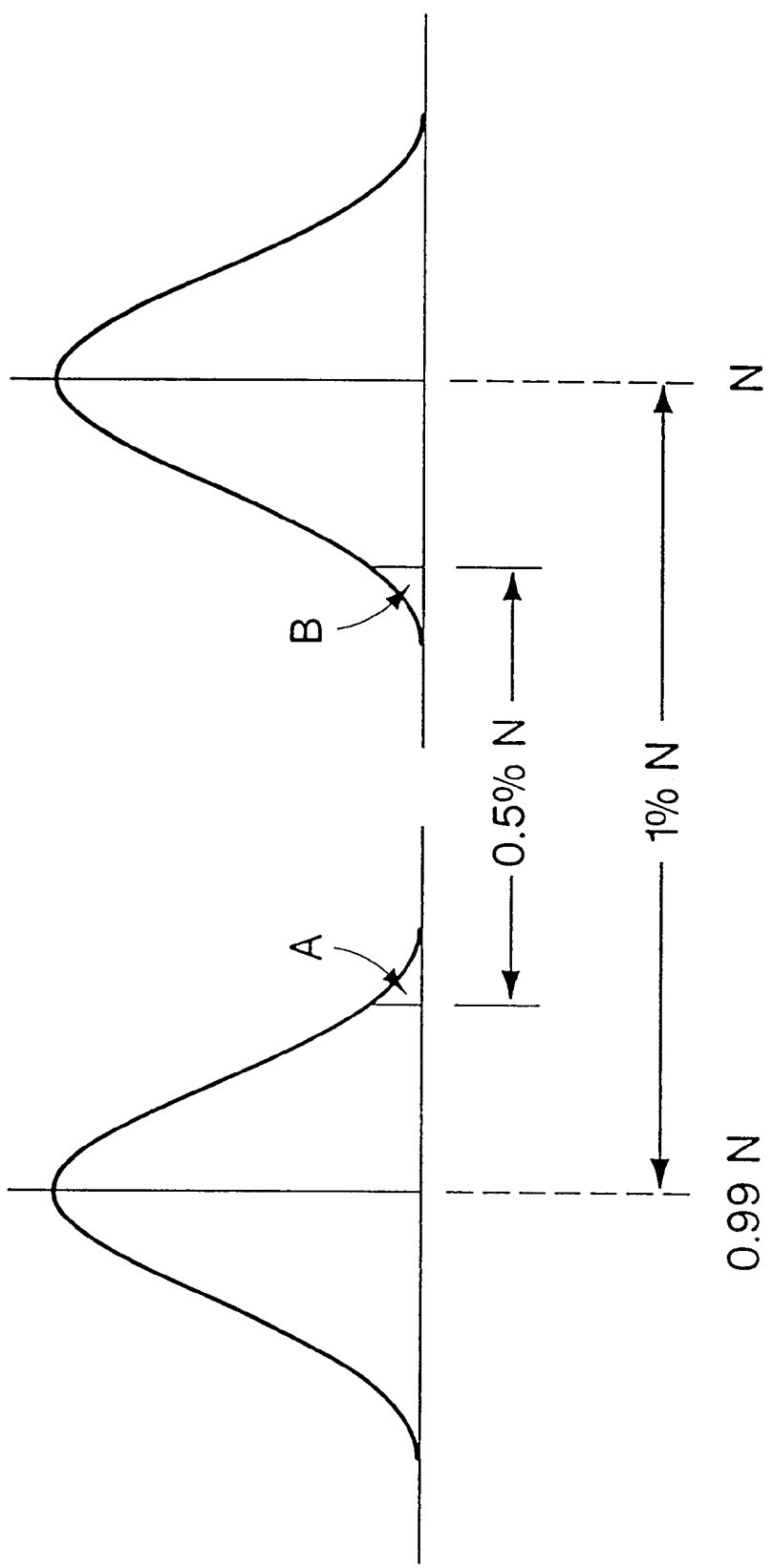
FIG. 3 is graph showing the probable values of N for a heterogeneous population of cells in which 1% of the cells are mutated.

To determine the minimum N required for 99% sensitivity a similar analysis is performed. This time, one-tailed Gaussian distribution tables show that 1.28 standard deviations (sigma) from the mean cover 90% of the Gaussian distribution. Moreover, there is a 10% (the square root of 1%) probability of one of the numbers (reference or target) being in either the area marked "A" in FIG. 3 or in the area marked "B" in FIG. 3. If the two population means are a total of 1% different and if there must be a 0.5% difference between the number of target and reference genes, then the distance from either mean to the threshold for statistical significance is equivalent to 0.25% N (See FIG. 3) for 99% sensitivity. As shown in FIG. 3, 0.25% N corresponds to about 40% of one side of the Gaussian distribution. Statistical tables reveal that 40% of the Gaussian distribution corresponds to 1.28 standard deviations from the mean. Therefore, 1.28 sigma is equal to 0.0025N, and N equals 262,144. Thus, for abnormal samples, the difference will exceed 0.5% at least 99% of the time if the lower of the two numbers is at least 262,144. Conversely, an erroneous negative diagnosis will be made only 1% of the time under these conditions.

In order to have both 99.9% specificity (avoidance of false positives) and 99% sensitivity (avoidance of false negatives), a sample with DNA derived from at least 553,536 (or roughly greater than 550,000) cells should be counted. A difference of at least 0.5% between the numbers obtained is significant at a confidence level of 99.0% for sensitivity and a difference of less than 0.5% between the numbers is significant at a confidence level of 99.9% for specificity. As noted above, other standard statistical tests may be used in order to determine statistical significance and the foregoing represents one such test.

Based upon the foregoing explanation, the skilled artisan appreciates that methods of the invention are useful to detect mutations in a subpopulation of a polynucleotides in any biological sample. For example, methods disclosed herein may be used to detect allelic loss (the loss of heterozygosity) associated with diseases such as cancer. Additionally, methods of the invention may be used to detect a deletion or a base substitution mutation causative of a metabolic error, such as complete or partial loss of enzyme activity. For purposes of exemplification, the following provides details of the use of methods according to the present invention in colon cancer detection. Inventive methods are especially useful in the early detection of a mutation (and especially a large deletion typical of loss of heterozygosity) in a tumor suppressor gene. Accordingly, while exemplified in the following manner, the invention is not so limited and the skilled artisan will appreciate its wide range of applicability upon consideration thereof.

Methods according to the invention preferably comprise comparing a number of a target polynucleotide known or suspected to be mutated to a number of a reference polynucleotide known or suspected not to be mutated. In addition to the alternative embodiments using either alleles or genetic loci as reference and target nucleic acids, the invention comprises a comparison of a microsatellite repeat region in a normal allele with the corresponding microsatellite region in an allele known or suspected to be mutated. Exemplary detection means of the invention comprise determining whether a difference exists between the number of counts of each nucleic acid being measured. The presence of a statistically-significant difference is indicative that a mutation has occurred in one of the nucleic acids being measured.

EXAMPLES

For purposes of exemplification, the following provides details of the use of methods according to the present invention in colon cancer detection. Inventive methods are especially useful in the early detection of a mutation. Accordingly, while exemplified in the following manner, the invention is not so limited and the skilled artisan will appreciate its wide range of applicability upon consideration thereof.

Exemplary Methods for Detection of Colon Cancer or Precancer

Example 1

Sample Preparation

In accordance with the present invention, the target nucleic acid represents a sample of nucleic acid isolated from a patient. This nucleic acid may be obtained from any cell source or body fluid. Non-limiting examples of cell sources available in clinical practice include blood cells, buccal cells, cervicovaginal cells, epithelial cells from urine, fetal cells, or any cells present in tissue obtained by biopsy. Body fluids include blood, urine, cerebrospinal fluid, and tissue exudates at the site of infection or inflammation.

In a preferred embodiment, the sample is a cross-sectional or circumferential portion of stool. Preferred methods for preparing a cross-sectional or circumferential portion of stool are provided in co-owned U.S. Pat. No. 5,741,650, and in co-owned co-pending patent application Ser. No. 09/059,713, incorporated by reference herein. As stool passes through the colon, it adheres cells and cellular debris sloughed from colonic epithelial cells. Similarly, cells and cellular debris are sloughed by a colonic polyp (comprising mutated DNA). However, only the portion of stool making contact with the polyp will adhere sloughed cells. It is therefore necessary to obtain at least a cross-sectional or circumferential portion of stool in order to ensure that the stool sample contains a mixture of all sloughed cells, including those sloughed by presumptive cancer cells (e.g., polyps).

After sample preparation, the sample is homogenized in an appropriate buffer, such as phosphate buffered saline comprising a salt, such as 20–100 mM NaCl or KCl, and a detergent, such as 1–10% SDS or Triton™, and/or a proteinase, such as proteinase K. An especially-preferred buffer is a Tris-EDTA-NaCl buffer as disclosed in co-owned, co-pending U.S. patent application Ser. No. 08/876,638, incorporated by reference herein. The buffer may also contain inhibitors of DNA and RNA degrading enzymes. Double-stranded DNA in the sample is melted (denatured to form single-stranded DNA) by well-known methods See, e.g., Gyllensten et al., in Recombinant DNA Methodology II, 565–578 (Wu, ed., 1995), incorporated by reference herein. DNA is then isolated from the cell source or body fluid using any of the numerous methods that are standard in the art. See, Smith-Ravin et al., Gut, 36: 81–86 (1995), incorporated by reference herein. It will be understood that the particular method used to extract DNA will depend on the nature of the source.

Once extracted, the target nucleic acid may be employed in the present invention without further manipulation. Alternatively, one or more specific regions present in the target nucleic acid may be amplified by PCR. In this case, the amplified regions are specified by the choice of particular flanking sequences for use as primers. Amplification at this step provides the advantage of increasing the concentration of specific nucleic acid sequences within the target nucleic acid sequence population.

In one embodiment, the target nucleic acid, with or without prior amplification of particular sequences, is bound to a solid-phase support. This allows the simultaneous processing and screening of a large number of patient samples. Non-limiting examples of supports suitable for use in the present invention include nitrocellulose or nylon filters, glass beads, magnetic beads coated with agents for affinity capture, treated or untreated microtiter plates, and the like. The conventional 96-well microtiter dishes used in diagnostic laboratories and in tissue culture are a preferred support. In a preferred embodiment, the support is a microtiter dish, having a multiplicity of wells. The use of such a support allows the simultaneous determination of a large number of samples and controls, and thus facilitates the analysis. Moreover, automated systems can be used to provide reagents to such microtiter dishes. It will be understood by a skilled practitioner that the method by which the target nucleic acid is bound to the support will depend on the particular matrix used. For example, binding of DNA to nitro-cellulose can be achieved by simple adsorption of DNA to the filter, followed by baking the filter at 75–80° C. under vacuum for 15 min–2 h. Alternatively, charged nylon membranes can be used that do not require any further treatment of the bound nucleic acid. Beads and microtiter plates that are coated with avidin or streptavidin can be used to bind target nucleic acid that has had biotin attached (via e.g. the use of biotin-conjugated PCR primers). In addition, antibodies can be used to attach target nucleic acids to any of the above solid supports by coating the surfaces with the antibodies and incorporating an antibody-specific hapten into the target nucleic acids. The target nucleic acids can also be attached directly to any of the above solid supports by epoxide/amine coupling chemistry. See Eggers et al. Advances in DNA Sequencing Technology, SPIE conference proceedings (1993). Once the nucleic acid samples are immobilized, the samples are washed to remove non-immobilized materials. The nucleic acid samples are then exposed to one or more set of segmented primers according to the invention. In an alternative embodiment, the nucleic acids remain in aqueous phase.

Example 2

Multiple Cycles of a Single Base Extension Reaction a) Primer Selection

Genomic regions suspected to contain one or more mutations are identified by reference to a nucleotide database, such as GenBank, EMBL, or any other appropriate database or publication, or by sequencing. For cancer detection, genetic mutations in a number of oncogenes and tumor suppressor genes are known. Duffy, Clin. Chem., 41: 1410–1413 (1993). Preferred genes for use in mutation detection methods of the invention include one or more oncogenes and/or one or more tumor suppressor genes. Specifically preferred genes include the ras oncogenes, p53, dcc, apc, mcc, and other genes suspected to be involved in the development of an oncogenic phenotype.

As will be described below, methods of the invention permit the detection of a mutation at a locus in which there is more than one nucleotide to be interrogated. Moreover, methods of the invention may be used to interrogate a locus in which more than one single base mutation is possible. Once regions of interest are identified, at least one primer is prepared to detect the presence of a suspected mutation. A primer of the invention preferably has a length from about 10 to about 100 nucleotides, more preferably between about 15 and about 35 nucleotides, and most preferably about 25 nucleotides.

The primer may be natural or synthetic, and may be synthesized enzymatically in vivo, enzymatically in vitro, or non-enzymatically in vitro. Primers for use in methods of the invention are preferably selected from oligodeoxyribonucleotides, oligoribonucleotides, copolymers of deoxyribonucleotides and ribonucleotides, peptide nucleic acids (PNAs), and other functional analogues. Peptide nucleic acids are well-known. See Pluskal, et al., The FASEB Journal, Poster #35 (1994). They are synthetic oligoamides comprising repeating amino acid units to which adenine, cytosine, guanine, thymine or uracil are attached. See Egholm, et al., Nature, 365: 566–568 (1993); Oerum, et al. Nucl. Acids Res., 23: 5332–36 (1993); Practical PNA: Identifying Point Mutations by PNA Directed PCR Clamping, PerSeptive Biosystems Vol. 1, Issue 1 (1995). Peptide nucleic acid synthons and oligomers are commercially available form PerSeptive Biosystems, Inc., Framingham, Mass. See, e.g., PCT publications EP 92/01219, EP 92/01220, U.S. Ser. No. 92/10921. In many applications, PNA probes are preferred to nucleic acid probes because, unlike nucleic acid/nucleic acid duplexes, which are destabilized under conditions of low salt, PNA/nucleic acid duplexes are formed and remain stable under conditions of very low salt. Additionally, because PNA/DNA complexes have a higher thermal melting point than the analogous nucleic acid/nucleic acid complexes, use of PNA probes can improve the reproducibility of blotting assays.

For exemplification, a primer designed to detect a mutation in the K-ras gene is provided below. According to methods of the invention, primers complementary to either portions of the coding strand or to portions of the non-coding strand may be used. For illustration, a primer useful for detection of mutations in the coding strand are provided below. Mutations in K-ras frequently occur in the codon for amino acid 12 of the expressed protein.

The wild-type codon 12 of the K-ras gene and its upstream nucleotides are:

wild-type template 3'-TATTTGAACACCATCAACCTC GACCA- 5' (SEQ ID NO: 1)

The three nucleotides encoding amino acid 12 are underlined. A primer (Primer 1) capable of interrogating the first nucleotide position in the codon encoding amino acid 12 of the K-ras gene is provided below.

Primer 1  5'-ATAAACTTGTGGTAGTTGGAGCT-3' (SEQ ID NO: 9)

b) Multiple Cycles of Primer Extension

Primer 1 is hybridized to a nucleic acid sample under conditions (see Tables 1 and 2) that promote selective binding of Primer 1 to the complementary sequence in the K-ras gene. The extension reaction is performed in the presence of the 4 different dideoxynucleotides ddATP, ddCTP, ddGTP, and ddTTP, each labeled with a different detectable label. The extension reaction is cycled 30 times as indicated in Table 2

| Component | Amount |
| --- | --- |
| H2O | 25.5 |
| 10X seq Buffer | 4 |
| ddNTP (50 uM) | 5 |
| Primer (5 uM) | 5 |
| Thermo Sequenase | 0.5 |
| DNA sample | 10 |

TABLE 2

Temperature profile for a cycled single base extension reaction

| Step | Temp. (C.) | Time (Sec.) |
| --- | --- | --- |
| 1 | 94 | 5 |
| 2 | 94 | 30 |
| 3 | 64 | 10 |
| 4 | 72 | 10 |
| 5 | Go to step 2, 29 times | |
| 6 | 4 | hold |

The reaction products are assayed for the incorporation of labeled ddNTPs. A nucleic acid sample containing wild-type DNA should only have labeled ddGTP incorporated. The incorporation of any other ddNTP in a statistically significant amount is indicative of the presence of a mutant K-ras nucleic acid in the sample.

Example 3

Preparation of Segmented Primers a) Primer Selection

Once regions of interest are identified, at least one segmented primer is prepared to detect the presence of a suspected mutation. A segmented primer comprises at least two oligonucleotide probes, a first probe and a second probe, which are capable hybridizing to substantially contiguous portions of a nucleic acid.

A first probe of the invention preferably has a length of from about 5 to about 10 nucleotides, more preferably between about 6 and about 8 nucleotides, and most preferable about 8 nucleotides. A second probe of the invention has a preferable length of between about 15 and 100 nucleotides, more preferably between about 15 and 30 nucleotides, and most preferably about 20 nucleotides. Further, a second probe is incapable of being a primer for template-dependent nucleic acid synthesis absent a first probe because it has a 3' terminal nucleotide that is non-extendible. Preferred non-extendible 3' terminal nucleotides include dideoxy nucleotides, C3 spacers, a 3' inverted base, biotin, or a modified nucleotide. Although, longer probes have a lower selectivity because of their tolerance of nucleotide mismatches, second probes are non-extendible and will not produce false priming in the absence of the proximal probe.

In an alternative embodiment, a segmented primer comprises a series of first probes, wherein each member of the series has a length of from about 5 to about 10 nucleotides, and most preferable about 6 to about 8 nucleotides. Although the first probes do not have a terminal nucleotide, nucleic acid extension will not occur unless all members of the series are hybridized to substantially contiguous portions of a nucleic acid.

The oligonucleotide probes of the segmented primer may be natural or synthetic, and may be synthesized enzymatically in vivo, enzymatically in vitro, or non-enzymatically in vitro. Probes for use in methods of the invention are preferably selected from oligodeoxyribonucleotides, oligoribonucleotides, copolymers of deoxyribonucleotides and ribonucleotides, peptide nucleic acids (PNAs), and other functional analogues. Peptide nucleic acids are well-known. See Pluskal, et al., The FASEB Journal, Poster #35 (1994). They are synthetic oligoamides comprising repeating amino acid units to which adenine, cytosine, guanine, thymine or uracil are attached. See Egholm, et al., Nature, 365: 566–568 (1993); Oerum, et al. Nucl. Acids Res., 23: 5332–36 (1993);

Practical PNA: Identifying Point Mutations by PNA Directed PCR Clamping, PerSeptive Biosystems Vol. 1, Issue 1 (1995). Peptide nucleic acid synthons and oligomers are commercially available form PerSeptive Biosystems, Inc., Framingham, Mass. See, e.g., PCT publications EP 92/01219, EP 92/01220, U.S. Ser. No. 92/10921. In many applications, PNA probes are preferred to nucleic acid probes because, unlike nucleic acid/nucleic acid duplexes, which are destabilized under conditions of low salt, PNA/ nucleic acid duplexes are formed and remain stable under conditions of very low salt. Additionally, because PNA/ DNA complexes have a higher thermal melting point than the analogous nucleic acid/nucleic acid complexes, use of PNA probes can improve the reproducibility of blotting assays.

For exemplification, segmented primers designed to detect mutations in the K-ras gene are provided below. According to methods of the invention, probes complementary to either portions of the coding strand or to portions of the non-coding strand may be used. For illustration, probes useful for detection of mutations in the coding strand are provided below. Mutations in K-ras frequently occur in the codon for amino acid 12 of the expressed protein. Several of the possible probes for detection of mutations at each of the three positions in codon 12 are shown below.

The wild-type codon 12 of the K-ras gene and its upstream nucleotides are:

wild-type template 3'-TATTTGAACACCATCAACCTC GACCA-5' (SEQ ID NO: 1)

The three nucleotides encoding amino acid 12 are underlined. First probes and second probes capable of interrogating the three nucleotides coding for amino acid 12 of the K-ras gene are provided below. First probe A is a first probe as described generally above, and has a sequence complementary to the nucleotides immediately upstream of the first base in codon 12 (i.e., immediately adjacent to the cytosine at codon position 1). Second probe A is a second probe as generally described above. It is complementary to a sequence that is substantially contiguous (here, exactly contiguous) with the sequence to which the first probe A is complementary. The bolded nucleotide in each of the second probes shown below is the nonextendible 3' terminal nucleotide. Hybridization of first and second probes suitable for detection of a mutation in the first base of K-ras codon 12 are shown below:

second probe A 5'-ATAAACTTGTGGTAG (SEQ ID NO: 2)

first probe A TTGGAGCT (SEQ ID NO: 3)

wild-type template 3'-TATTTGAACACCATCAACCT CGACCA-5' (SEQ ID NO: 1)

Detection of a mutation in the second base in codon 12 may be performed by using the same second probe as above (second probe A), and a first probe, identified as first probe B below, that is complementary to a sequence terminating immediately adjacent (3') to the second base of codon 12. Hybridization of probes suitable for detection of a mutation in the second base of codon 12 are shown below:

second probe A 5'-ATAAACTTGTGGTAG (SEQ ID NO: 2)

first probe B TGGAGCTG (SEQ ID NO: 4)

wild-type template 3'-TATTTGAACACCATCAACCTC GACCA-5' (SEQ ID NO: 1)

Detection of a mutation at the third position in codon 12 is accomplished using the same second probe as above, and first probe C, which abuts the third base of codon 12. Hybridization of probes suitable for detection of a mutation in the third base of codon 12 are shown below second probe A 5'-ATAAACTTGTGGTAG (SEQ ID NO: 2)

first probe C GGAGCTGG (SEQ ID NO: 6)

wild-type template 3'-TATTTGAACACCATCAACCT CGACCA -5'(SEQ ID NO: 1)

In methods for detection of mutations at the second and third nucleotides of codon 12 described above, the second probe is 1 and 2 nucleotides, respectively, upstream of the region to which the first probe hybridizes. Alternatively, second probes for detection of the second and third nucleotides of codon 12 may directly abut (i.e., be exactly contiguous with) their respective first probes. For example, an alternative second probe for detection of a mutation in the third base of codon 12 in K-ras is:

5'-ATAAACTTGTGGTAGTT (SEQ ID NO: 5)

The detection of mutations can also be accomplished with a segmented primer comprising a series of at least three first probes. A series of first probes suitable for detection of a mutation in the third base of codon 12 is shown below:

first probe X 5'-ATAAACTT (SEQ ID NO: 7)

first probe Y TGGTAGTT (SEQ ID NO: 8)

first probe Z GGAGCTGG (SEQ ID NO: 6)

wild-type template 3'-TATTTGAACACCATCAACCT CGACCA -6' (SEQ ID NO: 1)

b) Multiple Cycles of Primer Extension

First and second probes are exposed to sample under hybridization conditions that do not favor the hybridization of the short first probe in the absence of the longer second probe. Factors affecting hybridization are well known in the art and include raising the temperature, lowering the salt concentration, or raising the pH of the hybridization solution. Under unfavorable hybridization conditions (e.g., at a temperature 30–40° C. above first probe $T_m$), first probe forms an unstable hybrid when hybridized alone (i.e., not in the presence of a second probe) and will not prime the extension reaction. The longer, second probe, having a higher $T_m$, will form a stable hybrid with the template and, when hybridized to substantially contiguous portions of the nucleic acid, the second probe will impart stability to the shorter first probe, thereby forming a contiguous primer.

In a preferred embodiment, a modification of the dideoxy chain termination method as reported in Sanger, *Proc. Nat'l Acad. Sci.* (USA), 74: 5463–5467 (1977), incorporated by reference herein, is then used to detect the presence of a mutation. The method involves using at least one of the four common 2', 3'-dideoxy nucleoside triphosphates (ddATP, ddCTP, ddGTP, and ddTTP). A detectable detection moiety can be attached to the dideoxy nucleoside triphosphates (ddNTPs) according to methods known in the art. A DNA polymerase, such as Sequenase™ (Perkin-Elmer), is also added to the sample mixture. In a preferred embodiment, a thermostable polymerase, such as Taq or Vent DNA polymerase is added to the sample mixture. Using the substantially contiguous first and second probes as a primer, the polymerase adds one ddNTP to the 3' end of the first probe, the incorporated ddNTP being complementary to the nucleotide that exists at the single-base polymorphic site. Because the ddNTPs have no 3' hydroxyl, further elongation of the hybridized probe will not occur. Chain termination will also result where there is no available complementary ddNTP (or deoxynucleoside triphosphates) in the extension mixture. After completion of the single base extension reaction, extension products are isolated and detected.

Also in a preferred embodiment, labeled deoxynucleotides may be used for detection if either the extension reaction is stopped after addition of only one nucleotide or if only one labeled nucleotide, corresponding to the complement of the expected mutation, is exposed to the sample.

In the simplest embodiment of the invention, exemplified in Examples 2 and 3, the nucleoside triphosphate mixture contains just the labeled ddNTP or dNTP complementary to the known mutation. For example, to interrogate a sample for a C→A mutation in the first nucleotide of codon 12 of the K-ras gene, second probe A and first probe A are exposed to an extension reaction mixture containing labeled ddTTP or dTTP. The incorporation of a labeled ddTTP or dTTP in first probe A indicates the presence of a C→A mutation in the first nucleotide of codon 12 of the K-ras gene in the sample tested. First probe A co-hybridized with second probe A to a wild-type template will not be extended or, alternatively, will be extended with unlabeled ddGTP or dGTP if available in the reaction mixture.

Given the large number of mutations that have been associated with colorectal cancer, a detection method for this disease preferably screens a sample for the presence of a large number of mutations simultaneously in the same reaction (e.g., apc, K-ras, p53, dcc, MSH2, and DRA). As described above, only very limited multiplexing is possible with detection methods of the prior art. Since methods of the present invention eliminate false positive signals resulting from the tolerance of mismatches of the longer second probes, the use of segmented oligonucleotide avoids the need for optimization of hybridization conditions for individual probes and permits extensive multiplexing. Several segmented primers can be assayed in the same reaction, as long as the hybridization conditions do not permit stable hybridization of short first probes in the absence of the corresponding longer second probes.

In a preferred embodiment, the primer extension reactions are conducted in four separate reaction mixtures, each having an aliquot of the biological sample, a polymerase, and the three labeled complementary non-wild-type ddNTPs (or dNTPs). Optionally, the reaction mixtures may also contain the unlabeled complementary wild-type ddNTP (or dNTP). The segmented primers are multiplexed according to the wild-type template. In the present exemplification, the first two nucleotides coding for amino acid 12 of the K-ras gene are cysteines. Accordingly, second probe A and first probes A and B are added to a reaction mixture containing labeled ddATP (or dATP), ddTTP (or dTTP), and ddCTP (or dCTP). Second probe C and first probe C are added to a reaction mixture containing labeled ddATP (or dATP), ddCTP (or dCTP), and ddGTP (or dGTP). Any incorporation of a labeled ddNTP in a first probe indicates the presence of a mutation in codon 12 of the K-ras gene in the sample. This embodiment is especially useful for the interrogation of loci that have several possible mutations, such as codon 12 of K-ras.

In an alternative preferred embodiment, the primer extension reactions are conducted in four separate reaction mixtures, each containing only one labeled complementary non-wild-type ddNTP or dNTP and, optionally, the other three unlabeled ddNTPs or dNTPs. Segmented primers can be thus be exposed only to the labeled ddNTP or dNTP complementary to the known mutant nucleotide or, alternatively, to all three non-wild-type labeled ddNTPs or dNTPs. In the K-ras example provided above, if the first nucleotide of K-ras codon 12 is interrogated for a known C→G mutation, first probe A and second probe A are added to only one reaction mixture, the reaction mixture containing labeled ddCTP (or dCTP). Optionally, methods of the invention may be practiced as described above using labeled deoxynucleotides.

However, since several mutations have been identified at codon 12 of the K-ras gene, the probes are exposed to all non-wild-type labeled ddNTPs or dNTPs. Thus, second probe A and first probes A and B are added to the three reaction mixtures containing labeled ddATP (or dATP), ddTTP (or dTTP), or ddCTP (or dCTP). Second probe C and first probe C are added to the three reaction mixtures containing one of labeled ddATP (or dATP), ddCTP (or dCTP), and ddGTP (or dGTP). Again, the extension of a first probe with a labeled terminal nucleotide indicates the presence of a mutation in codon 12 of the K-ras gene in the biological sample tested.

In a preferred embodiment, several cycles of extension reactions are conducted in order to amplify the assay signal. Extension reactions are conducted in the presence of an excess of first and second probes, labeled dNTPs or ddNTPs, and heat-stable polymerase. Once an extension reaction is completed, the first and second probes bound to target nucleic acids are dissociated by heating the reaction mixture above the melting temperature of the hybrids. The reaction mixture is then cooled below the melting temperature of the hybrids and first and second probes permitted to associate with target nucleic acids for another extension reaction. In a preferred embodiment, 10 to 50 cycles of extension reactions are conducted. In a most preferred embodiment, 30 cycles of extension reactions are conducted.

Example 4

Methods for Identification of Genetic Alterations

In one embodiment, the labeled primers or probes are immobilized as described herein, and are directly subjected to sequencing, using a chemical method standard in the art (e.g., Maxam-Gilbert sequencing, Maxam and Gilbert, 1977, *Proc. Natl. Acad. Sci., USA*, 74:560).

In other embodiments, the immobilized labeled primers or first probes are removed from the solid support and sequencing of labeled first probes is performed in aqueous solution. In one embodiment, the sequence of the labeled first probes is determined by sequence-specific reverse hybridization by exposing the labeled first probes to oligonucleotides corresponding to each of the multiple sequences being interrogated in the assay. Hybridization analysis can be accomplished by several methods known in the art, such as dot blots. See, Ausubel et al., *Short Protocols in Molecular Biology*, 3rd ed. (John Wiley & Sons, Inc., 1995). In a preferred embodiment, the oligonucleotides are immobilized to a solid support at defined locations (i.e., known positions). This immobilized array is sometimes referred to as a "DNA chip." The solid support can be a plate or chip of glass, silicon, or other material. The solid support can also be coated (e.g., with gold or silver) to facilitate attachment of the oligonucleotides to the surface of the solid support. Any of a variety of methods known in the art may be used to immobilize oligonucleotides to a solid support. A commonly used method consists of the non-covalent coating of the solid support with avidin or streptavidin and the immobilization of biotinylated oligonucleotide probes. The oligonucleotides can also be attached directly to the solid supports by epoxide/amine coupling chemistry. See Eggers et al. Advances in DNA Sequencing Technology, SPIE conference proceedings (1993).

In another embodiment, the sequence of the labeled first probe is read by the hybridization and assembly of positively hybridizing probes through overlapping portions. Drmanac et al., U.S. Pat. No. 5,202,231, incorporated herein by reference.

In yet another embodiment, first probes extended by a labeled dNTP are identified by enzymatic DNA sequencing (Sanger et al., 1977, *Proc. Natl. Acad. Sci., USA*, 74:5463). In this case, oligonucleotides are synthesized that contain DNA sequences complementary to the first probes and additional pre-determined co-linear sequences that act as sequence "tags." When incubated under Sanger sequencing conditions, the immobilized first probes hybridize to their complementary sequences and act as primers for the sequencing reaction. Determination of the resulting primed sequence "tag" then identifies the first probe(s) present in the reaction.

In a further embodiment, first probes extended by a labeled dNTP are amplified prior to the sequence identification. Labeled first probes are incubated with complementary oligonucleotides that contain a sequencing primer sequence with or without an additional "tag". Initial hybridization of a first probe to its complementary oligonucleotide allows the first probe to serve as the initial primer in a single extension reaction. The extension product is then used directly as template in a cycle sequencing reaction. Cycle sequencing of the extension products results in amplification of the sequencing products. In designing the complementary oligonucleotides, the sequencing primer is oriented so that sequencing proceeds through the first probe itself, or, alternatively, through the "tag" sequence. In the latter case, the determination of the "tag" sequence will identify the colinear first probe sequence. The amplified products are sequenced by a chemical method standard in the art or identified by sequence-specific reverse hybridization methods, as described above.

In practicing the present invention, it is not necessary to determine the entire sequence of the first probe or of the complementary tagged oligonucleotide. It is contemplated that 1, 2, or 3 sequencing reactions (instead of the four needed to obtain a complete sequence) will be effective in producing characteristic patterns (similar to "bar codes") to allow the immediate identification of the individual first probes. This approach is applicable to manual sequencing methods using radioactively labeled first probes, which produce analog or digitized autoradiograms, as well as to automated sequencing methods using non-radioactive reporter molecules, which produce digitized patterns. In either case, comparisons to an established data base can be performed electronically. Thus, by reducing the number of required sequencing reactions, the methods of the present invention facilitate the economical analysis of multiple samples.

The present invention accommodates the simultaneous screening of a large number of potential first probes in a single reaction. In practice, the actual number of segmented primers that are pooled for simultaneous hybridization is determined according to the diagnostic need. For example, in cystic fibrosis (CF), one particular mutation (Δ508) accounts for more than 70% of CF cases. This, a preliminary screening with a Δ508-specific segmented primers according to the present methods, followed by single base extension of the contiguous primers, and detection of the extended first probes, will identify and eliminate Δ508 alleles. In a second ("phase two") screening, a large number of segmented primers encoding other, less frequent, CF alleles is performed, followed by single base extension of the contiguous primers, and detection of the extended first probes as described above.

In other clinical situations, however, a single mutation that appears with as high a frequency as the Δ508 mutation in CF does not exist. Therefore, pools of segmented primers are determined only by the number of independent assays that would be needed in a phase two analysis on a pool positive sample.

In addition, in current clinical practice, different clinical syndromes, e.g. cystic fibrosis, thalassemia, and Gaucher's disease, are screened independently of each other. The present invention, by contrast, accommodates the simultaneous screening of large numbers of nucleic acids from different patients with a large number of first probes that are complementary to mutations in more than one potential disease-causing gene.

In the same manner, when clinical indicators suggest infection by a foreign agent or microorganism, the present invention provides for simultaneous screening for a large number of potential foreign nucleic acids. Furthermore, particular strains, variants, mutants, and the like of one or more microorganisms can also be distinguished by employing appropriate first probes in the first screening.

The methods of the present invention also make it possible to define potentially novel mutant alleles carried in the nucleic acid of a patient or an invading microorganism, by the use of randomly permuted segmented primers in phase one or phase two screening. In this embodiment, single base extension of contiguous primers and detection and isolation of extended first probes, followed by sequencing, reveals the precise mutant sequence.

The foregoing exemplifies practice of the invention in the context of multiple mutation detection using segmented primers. As disclosed herein, numerous additional aspects and advantages of the invention are apparent upon consideration of the disclosure and the specific exemplification. Accordingly, the invention is limited only by the scope of the appended claims.

What is claimed is:

1. A method for identifying a single nucleotide in a nucleic acid sample, the method comprising the steps of:
   (a) annealing an oligonucleotide primer to a nucleic acid sample under conditions that promote exact complementary hybridization between said primer and a portion of a nucleic acid in said sample;
   (b) extending said primer by a single base, wherein said extension reaction is performed in an extension solution comprising at least two different nucleotides;
   (c) separating said extended primer from said portion;
   (d) repeating steps (a) through (c) at least once; and
   (e) identifying said base incorporated into said extended primer in step (b), thereby to identify said single nucleotide.

2. The method of claim 1, wherein said extension reaction in step (b) is performed in the presence of one or more chain-terminating nucleotides.

3. The method of claim 1, wherein said single base is detectably labeled.

4. The method of claim 1, wherein said single nucleotide is a polymorphic variant.

5. The method of claim 1, wherein said sample comprises nucleic acid pooled from a plurality of tissue or body fluid specimens from different individuals.

6. The method of claim 1, wherein said sample of nucleic acid is heterogeneous.

7. The method of claim 1, wherein in said annealing step an excess concentration of said oligonucleotide primer is used.

8. The method of claim 1, wherein said nucleic acid sample in step (a) has been subjected to a prior amplification step.

9. The method of claim 1, wherein, in step (a), nucleic acids in said nucleic acid sample are bound to a solid-phase support.

10. The method of claim 1, wherein, in step (a), two or more oligonucleotide primers are added, each of said two or more primers promoting hybridization to a different portion of a nucleic acid in said sample.

11. The method of claim 1, wherein, in step (b), said extension reaction is performed in the presence of four different nucleotides.

12. The method of claim 1, wherein, in step (b), said nucleotides are deoxynucleotides.

13. A method for identifying a single nucleotide in a nucleic acid sample, the method comprising the steps of:
   (a) annealing an oligonucleotide primer to a nucleic acid sample, wherein said primer is a segmented primer comprising two or more probes, wherein none of said probes alone is capable of serving as a primer for template-dependent extension but wherein, when said two or more probes anneal to said nucleic acid sample adjacent to each other, they are capable of priming template-dependent extension;
   (b) extending said primer by a single base;
   (c) separating said extended primer from said portion;
   (d) repeating steps (a) through (c) at least once; and
   (e) identifying said base incorporated into said extended primer in step (b), thereby to identify said single nucleotide.

14. The method of claim 13, wherein said segmented primer comprises one probe having less than 15 nucleotides and one probe having greater than or equal to 15 nucleotides.

15. The method of claim 13, wherein said segmented primer comprises three or more probes, each said probe having fewer than 15 nucleotides.

16. A method for detecting the presence of a known single nucleotide polymorphic variant, said method comprising the steps of:
   (a) annealing an oligonucleotide primer to a portion of a nucleic acid suspected to be immediately upstream of a single nucleotide polymorphic variant;
   (b) extending said primer by a single base, wherein said extension reaction is performed in an extension solution comprising at least two different nucleotides;
   (c) separating said primer from said nucleic acid;
   (d) repeating steps (a) through (c) at least once; and
   (e) identifying said single base, thereby to identify the polymorphic variant.

17. The method of claim 16, wherein said single nucleotide polymorphic variant is indicative of disease.

18. The method of claim 17, wherein said disease is selected from the group consisting of cancer, cystic fibrosis, tay-sachs, sickle cell anemia, Gaucher's disease, B-thalassemia, and parasitic infections.

19. A method for identifying a single nucleotide polymorphic variant in a population, said method comprising the steps of:
   (a) obtaining a sample comprising nucleic acid from each member of a plurality of individuals in a population;
   (b) annealing an oligonucleotide primer to a portion of said nucleic acid in each sample, said primer being complementary to a portion of the nucleic acid immediately upstream of a suspected single nucleotide polymorphic variant;

(c) extending said primer in each sample by a single base, wherein said extension reaction is performed in an extension solution comprising at least two different nucleotides;

(d) separating said primer from said nucleic acid in each sample;

(e) repeating steps (b) through (d) at least once;

(f) identifying said single base in each sample; and (g) identifying a single nucleotide polymorphic variant as the presence of more than one base identified in step (f).

20. The method of claim 19, wherein said samples are combined and said method is carried out on said combined samples.

21. A method for detecting the presence of a target nucleotide at a genetic locus of interest, said method comprising the steps of:

(a) obtaining a sample comprising heterogeneous nucleic acid;

(b) annealing an oligonucleotide primer to a portion of a nucleic acid suspected to be immediately upstream of a target nucleotide at a genetic locus of interest;

(c) extending said primer in the presence of a labeled nucleotide that is complementary to said target nucleotide;

(d) further extending said primer in the presence of a terminator nucleotide, thereby to generate an extension product;

(e) separating said primer from said nucleic acid;

(f) repeating steps (b) through (e) at least once; and (g) determining whether said labeled nucleotide is present in said extension product, thereby to determine whether said target nucleotide is present at said genetic locus.

22. The method of claim 21, wherein, in step (c), said labeled nucleotide is a deoxynucleotide and, in step (d), said terminator nucleotide is a dideoxynucleotide.

23. The method of claim 21, wherein, in step (c), only one species of labeled nucleotide is present.

24. A method for detecting the presence of a target single nucleotide polymorphic variant at a genetic locus of interest, said method comprising the steps of:

(a) obtaining a sample comprising heterogeneous nucleic acid;

(b) annealing an oligonucleotide primer to a portion of a nucleic acid suspected to be immediately upstream of a target single nucleotide polymorphic variant position;

(c) extending said primer in the presence of a labeled nucleotide that is complementary to a nucleotide suspected to be present at said target position;

(d) further extending said primer in the presence of an unlabeled terminator nucleotide, thereby to generate an extension product;

(e) separating said primer from said nucleic acid;

(f) repeating steps (b) through (e) at least once; and (g) determining whether said labeled nucleotide is present in said extension product, thereby to determine whether said target single nucleotide polymorphic variant is present at said genetic locus.

* * * * *

SEQUENCE LISTING

<160> NUMBER OF SEQ ID NOS: 9

<210> SEQ ID NO 1
<211> LENGTH: 26
<212> TYPE: DNA
<213> ORGANISM: Artificial Sequence
<220> FEATURE:
<223> OTHER INFORMATION: Sequencing reaction probe/primer

<400> SEQUENCE: 1
accagctcca actaccacaa gtttat

```
<210> SEQ ID NO 2
<211> LENGTH: 15
<212> TYPE: DNA
<213> ORGANISM: Artificial Sequence
<220> FEATURE:
<223> OTHER INFORMATION: Sequencing reaction probe/primer

<400> SEQUENCE: 2
ataaacttgt ggtag                                                    15

<210> SEQ ID NO 3
<211> LENGTH: 8
<212> TYPE: DNA
<213> ORGANISM: Artificial Sequence
<220> FEATURE:
<223> OTHER INFORMATION: Sequencing reaction probe/primer

<400> SEQUENCE: 3 ttggagct                                                             8

<210> SEQ ID NO 4
<211> LENGTH: 8
<212> TYPE: DNA
<213> ORGANISM: Artificial Sequence
<220> FEATURE:
<223> OTHER INFORMATION: Sequencing reaction probe/primer

<400> SEQUENCE: 4 tggagctg                                                             8

<210> SEQ ID NO 5
<211> LENGTH: 17
<212> TYPE: DNA
<213> ORGANISM: Artificial Sequence
<220> FEATURE:
<223> OTHER INFORMATION: Sequencing reaction probe/primer

<400> SEQUENCE: 5
ataaacttgt ggtagtt                                                  17

<210> SEQ ID NO 6
<211> LENGTH: 8
<212> TYPE: DNA
<213> ORGANISM: Artificial Sequence
<220> FEATURE:
<223> OTHER INFORMATION: Sequencing reaction probe/primer

<400> SEQUENCE: 6 ggagctgg                                                             8

<210> SEQ ID NO 7
<211> LENGTH: 8
<212> TYPE: DNA
<213> ORGANISM: Artificial Sequence
<220> FEATURE:
<223> OTHER INFORMATION: Sequencing reaction probe/primer

<400> SEQUENCE: 7 ataaactt                                                             8

<210> SEQ ID NO 8
<211> LENGTH: 8
<212> TYPE: DNA
<213> ORGANISM: Artificial Sequence
<220> FEATURE:
```

```
<223> OTHER INFORMATION: Sequencing reaction probe/primer

<400> SEQUENCE: 8 tggtagtt                                                                          8

<210> SEQ ID NO 9
<211> LENGTH: 23
<212> TYPE: DNA
<213> ORGANISM: Artificial Sequence
<220> FEATURE:
<223> OTHER INFORMATION: Sequencing reaction probe/primer

<400> SEQUENCE: 9
ataaacttgt ggtagttgga gct                                                         23
```